United States Patent
Sun et al.

(10) Patent No.: US 10,814,299 B2
(45) Date of Patent: Oct. 27, 2020

(54) LOADING NUCLEIC ACIDS ONTO SUBSTRATES

(71) Applicant: Pacific Biosciences of California, Inc., Menlo Park, CA (US)

(72) Inventors: Lei Sun, San Jose, CA (US); Jaime Juan Benitez-Marzan, Fremont, CA (US); Natasha Popovich, Belmont, CA (US); Sassan Sheikholeslami, San Francisco, CA (US); Steven Lin, Palo Alto, CA (US); Aparna Vedula, Redwood City, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 358 days.

(21) Appl. No.: 15/354,812

(22) Filed: Nov. 17, 2016

(65) Prior Publication Data
US 2017/0136433 A1 May 18, 2017

Related U.S. Application Data

(60) Provisional application No. 62/413,313, filed on Oct. 26, 2016, provisional application No. 62/396,637, filed on Sep. 19, 2016, provisional application No. 62/257,152, filed on Nov. 18, 2015.

(51) Int. Cl.
| | | |
|---|---|---|
| *C12P 19/34* | (2006.01) | |
| *B01J 19/00* | (2006.01) | |
| *C12Q 1/6806* | (2018.01) | |

(52) U.S. Cl.
CPC ........ *B01J 19/0046* (2013.01); *C12Q 1/6806* (2013.01); *B01J 2219/00317* (2013.01); *B01J 2219/00637* (2013.01); *B01J 2219/00648* (2013.01); *B01J 2219/00659* (2013.01); *B01J 2219/00709* (2013.01); *B01J 2219/00722* (2013.01)

(58) Field of Classification Search
None
See application file for complete search history.

(56) References Cited

U.S. PATENT DOCUMENTS

| | | |
|---|---|---|
| 6,917,726 B2 | 7/2005 | Levene et al. |
| 7,033,764 B2 | 4/2006 | Korlach et al. |
| 7,052,847 B2 | 5/2006 | Korlach et al. |
| 7,056,661 B2 | 6/2006 | Korlach et al. |
| 7,056,676 B2 | 6/2006 | Korlach et al. |
| 7,292,742 B2 | 11/2007 | Levene et al. |
| 7,302,146 B2 | 11/2007 | Turner et al. |
| 7,315,019 B2 | 1/2008 | Turner et al. |
| 7,833,398 B2 | 11/2010 | Craighead et al. |
| 7,907,800 B2 | 3/2011 | Foquet et al. |
| 8,153,375 B2 | 4/2012 | Travers et al. |
| 8,236,499 B2 | 8/2012 | Patel et al. |
| 8,481,264 B2 | 7/2013 | Bjornson et al. |
| 8,715,930 B2 | 5/2014 | Pham et al. |
| 8,802,600 B2 | 8/2014 | Rank et al. |
| 8,906,670 B2 | 12/2014 | Gray et al. |
| 8,906,831 B2 | 12/2014 | Eid et al. |
| 8,993,307 B2 | 3/2015 | Zaccarin et al. |
| 8,994,946 B2 | 3/2015 | McCaffrey et al. |
| 9,116,118 B2 | 8/2015 | Turner et al. |
| 9,381,517 B2 | 7/2016 | Pham et al. |
| 9,399,766 B2 | 7/2016 | Kamtekar et al. |
| 2003/0044781 A1 | 3/2003 | Korlach et al. |
| 2008/0032301 A1 | 2/2008 | Rank et al. |
| 2009/0298075 A1 | 12/2009 | Travers et al. |
| 2010/0009872 A1* | 1/2010 | Eid .................. G01N 33/54313 506/26 |
| 2010/0261158 A1 | 10/2010 | Nordman et al. |
| 2011/0281776 A1* | 11/2011 | Eshoo .................. B01L 3/5027 506/40 |
| 2012/0071359 A1 | 3/2012 | Sun et al. |
| 2012/0322692 A1* | 12/2012 | Pham .................. C12Q 1/6869 506/26 |
| 2013/0116153 A1* | 5/2013 | Bowen ................. B01J 19/0046 506/16 |
| 2013/0178369 A1 | 7/2013 | Burns et al. |
| 2013/0327644 A1 | 12/2013 | Turner et al. |
| 2014/0051068 A1 | 2/2014 | Cherf et al. |
| 2014/0094375 A1 | 4/2014 | Kamtekar et al. |
| 2015/0080228 A1 | 3/2015 | Luo et al. |
| 2015/0125854 A1 | 5/2015 | Fedorov et al. |
| 2016/0310926 A1 | 10/2016 | Sun et al. |
| 2017/0159119 A1 | 6/2017 | Sheikholeslami et al. |

FOREIGN PATENT DOCUMENTS

| | | | |
|---|---|---|---|
| WO | 1996021036 | 7/1996 | |
| WO | 2007075987 A2 | 7/2007 | |
| WO | 2007076057 A2 | 7/2007 | |
| WO | 2007123763 A2 | 11/2007 | |
| WO | WO-2010115016 A2 * | 10/2010 | ......... C12N 15/1006 |
| WO | 2011026102 A1 | 3/2011 | |
| WO | 2018118992 A1 | 6/2018 | |

OTHER PUBLICATIONS

Bai et al., "Critical Assessment of Nucleic Acid Electrostatics via Experimental and Computational Investigation of an Unfolded State Ensemble" J. Am. Chem. Soc. (2008) 130(37):pp. 12334-12341.
Bloomfield, "DNA Condensation by Multivalent Cations," Biopolymers (1997) 44(3):269-82.
Bloomfield, DNA Condensation, Current Opinion in Structural Biology (1996) 6:334-341.
Cheng et al., "Polyethylene glycol and divalent salt-induced DNA reentrant condensation revealed by single molecule measurements," Soft Matter (2015) 11:3927-3935.
Cinque et al., "Protection of Human Genomic DNA from Mechanical Stress by Reversible Folding Transition," ChemBioChem (2010) 11:340-343.

(Continued)

*Primary Examiner* — Kenneth R Horlick
(74) *Attorney, Agent, or Firm* — Monicia Elrod-Erickson

(57) ABSTRACT

Methods, compositions, and systems for distributing nucleic acids into array regions are provided. The methods, compositions, and systems utilize nucleic acid condensing agents to increase efficiency of distribution of the nucleic acids into the array regions. Various methods for facilitating distribution of the nucleic acids to the array regions are provided.

23 Claims, 8 Drawing Sheets

(56) References Cited

OTHER PUBLICATIONS

Driscoll et al., "Atomic-Scale Imaging of DNA Using Scanning Tunneling Microscopy," Nature (1990) 346(6281):294-296.
Eid et al., "Real-Time DNA Sequencing From Single Polymerase Molecules," Science (2009) 323:133-138.
Estevez-Torresa and Damien Baigl, "DNA Compaction: Fundamentals and Applications," SoftMatter (2011) 7:6746.
Foquet et al., "Improved Fabrication of Zero-Mode Waveguides for Single-Molecule Detection," Journal of Applied Physics (2008) 103:034301.
Goodwin et al., "Application of Single Molecule Detection to DNA Sequencing," Nucleosides & Nucleotides (1997) 16(5-6):543-550.
Howorka et al., "Sequence-Specific Detection of Individual DNA Strands using Engineered Nanopores," Nature Biotechnology (2001) 19(7): 636-639.
Korlach et al., "Long, Processive Enzymatic DNA Synthesis Using 100% Dye-Labeled Terminal Phosphate-Linked Nucleotides," Nucleosides, Nucleotides and Nucleic Acids (2008) 27:1072-1083.
Korlach et al., "Selective Aluminum Passivation for Targeted Immobilization of Single DNA Polymerase Molecules in Zero-Mode Waveguide Nanostructures," PNAS (2008) 105(4):1176-1181.
Lerman, "A Transition to a Compact Forum of DNA in Polymer Solutions," Proc. Natl. Acad. Sci. (1971) 68:1886-1890.
Levene et al., "Zero-mode Waveguides for Single-molecule Analysis at High Concentration" Science (2003) 299:682-686.
Lis and Schleif, "Size Fractionation of Double-Stranded DNA by Precipitation with Polyethylene Glycol" Nucleic Acids Res. (1975) 2(3):383-9.
Lis, "Fractionation of DNA Fragments by Polyethylene Glycol Induced Precipitation," Methods Enzymol. (1980) 65(1):347-53.
Meller et al., "Rapid Nanopore Discrimination Between Single Polynucleotide Molecules," Proceedings of the National Academy of Sciences of the United States of America (2000) 97(3): 1079-1084.
Rigler et al., "DNA-Sequencing at the Single Molecule Level," Journal of Biotechnology (2001) 86(3):161.
Teif, "Condensed DNA: Condensing the Concepts," Progress in Biophysics and Molecular Biology (2011) 105:208-222.
Travers et al., "A Flexible and Efficient Template Format for Circular Consensus Sequencing and SNP Detection," Nucl. Acids Res. (2010) 38(15):e159.
Vasilevskaya et al., "Collapse of Single DNA Molecule in Poly(Ethylene Glycol) Solutions," The Journal of Chemical Physics Volume (1995) 102: 6595-6602.
Yoshikawa et al., "Highly Effective Compaction of Long Duplex DNA Induced by Polyethylene Glycol with Pendant Amino Groups," J. Am. Chem. Soc. (2010) 119:6473-6477.
Yu et al., "A Compact Form of Double-Stranded DNA in Solution," FEBS Letters (1972) 23(2):180-184.
International Preliminary Report on Patentability dated May 31, 2018 for related PCT/US2016/062582.
International Search Report and Written Opinion dated Mar. 24, 2017 for related PCT/US2016/062582.
EP Search Report dated Feb. 27, 2019 for related EP16867159.2.
First Exam Report dated Oct. 8, 2019 for related EP16867159.2.

* cited by examiner

| Sample | Total reads | Empty(P0) | Productive P1(+) | Other P2(+) |
|---|---|---|---|---|
| 11k-C2v2-5pM | 28308 | 117274 (78%) | 28308 (19%) | 4710 (3%) |
| 11k-P18-5pM | 65238 | 69372 (46%) | 65238 (43%) | 15682 (10%) |

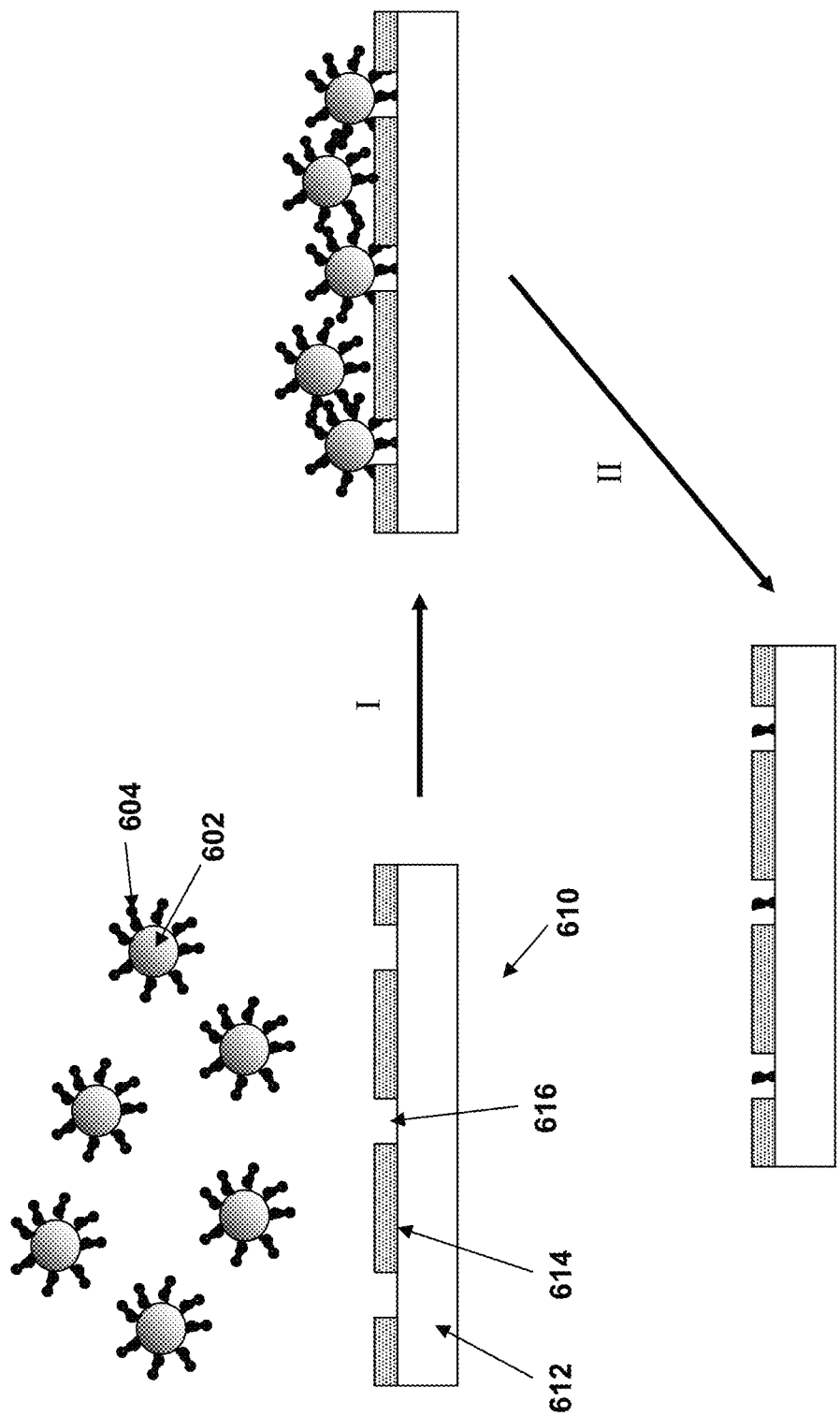

LOADING NUCLEIC ACIDS ONTO SUBSTRATES

CROSS-REFERENCE TO RELATED APPLICATIONS

This application is a non-provisional utility patent application claiming priority to and benefit of the following prior provisional patent applications: U.S. Ser. No. 62/413,313, filed Oct. 26, 2016, entitled "LOADING NUCLEIC ACIDS ONTO SUBSTRATES" by Lei Sun et al., U.S. Ser. No. 62/396,637, filed Sep. 19, 2016, entitled "LOADING NUCLEIC ACIDS ONTO SUBSTRATES" by Lei Sun et al., and U.S. Ser. No. 62/257,152, filed Nov. 18, 2015, entitled "METHODS AND COMPOSITIONS FOR LOADING OF POLYMERASE COMPLEXES" by Sassan Sheikholeslami et al., each of which is incorporated herein by reference in its entirety for all purposes.

BACKGROUND OF THE INVENTION

Techniques in molecular biology and molecular medicine often rely on analysis of single biological molecules. Such techniques include DNA and RNA sequencing, polymorphism detection, detection of proteins of interest, detection of protein-nucleic acid complexes, and many others. The high sensitivity, high throughput, and low reagent costs involved in single molecule analysis make this type of analysis an increasingly attractive approach for a variety of detection and analysis problems in molecular medicine, from low cost genomics to high sensitivity marker analysis.

The small observation volumes often used for single molecule analysis methods are typically provided by immobilizing or otherwise localizing molecules of interest within optical confinement reaction/observation regions, such as an array of extremely small wells as in an array of Zero Mode Waveguides (ZMWs) or other nanoscale wells. However, entropic barriers to loading can be significant when attempting to load large reactant molecules (e.g., large nucleic acid template-polymerase complexes) into nanoscale reaction sites.

Methods for increasing the efficiency of loading (for example, increasing the number of wells productively loaded, decreasing the amount of sample required for loading, and/or decreasing the time required for loading) are therefore desirable. The invention described herein fulfills these and other needs, as will be apparent upon review of the following.

SUMMARY OF THE INVENTION

In some aspects, the invention provides methods for distributing nucleic acid molecules into a plurality of array regions. In the methods, a surface comprising the plurality of array regions is provided and exposed to a solution comprising the nucleic acid molecules and a nucleic acid condensing agent. In some embodiments, the nucleic acid condensing agent comprises a polyethylene glycol polymer. In some embodiments, the nucleic acid condensing agent comprises polyethylene glycol (PEG) and a salt comprising a cation.

Provision of the condensing agent can facilitate loading of large nucleic acids into the array regions. Thus, in some embodiments, the nucleic acids are at least about 10 kb in length, at least about 20 kb in length, at least about 30 kb in length, or at least about 40 kb in length. In some embodiments, the nucleic acid molecules are part of protein-nucleic acid complexes, for example, polymerase-template complexes or helicase-nucleic acid complexes. Optionally, the nucleic acid molecules are immobilized in the array regions. In some embodiments, the array regions comprise nanoscale wells, for example, zero mode waveguides (ZMWs). In other embodiments, the array regions comprise nanopores.

Essentially all of the features noted for other embodiments herein apply to these embodiments as well, as relevant.

In some aspects, the invention provides methods for distributing nucleic acid molecules into a plurality of array regions. In the methods, a surface comprising the plurality of array regions is provided and exposed to a solution comprising the nucleic acid molecules, polyethylene glycol (PEG), and a salt comprising a cation. In some embodiments, the nucleic acid molecules are the templates in polymerase-template complexes that are distributed into the array regions.

A variety of PEGs are known in the art and are suitable for use in the methods. In one class of embodiments, the solution comprises PEG 8000, for example, at a concentration of 2.5-25 mM or 5-15 mM. The cation can be, e.g., a monovalent or divalent cation. In one class of embodiments, the solution comprises a monovalent cation, e.g., at a concentration of 50 to 500 mM or 100 to 300 mM, e.g., $Na^+$ or $K^+$. In one class of embodiments, the solution comprises a divalent cation, e.g., at a concentration of 0.05 to 10 mM, e.g., $Sr^{2+}$. Combinations of cations can also be employed, e.g., $K^+$ and $Sr^{2+}$. In one exemplary class of embodiments, the solution comprises PEG 8000 and K+, e.g., 5-15 mM PEG 8000 and 100-300 mM $K^+$. In one exemplary class of embodiments, the solution comprises PEG 8000, $K^+$, and $Sr^{2+}$, e.g., 5-15 mM PEG 8000, 100-300 mM $K^+$, and 0.05-0.3 mM $Sr^{2+}$.

In some embodiments, the array regions comprise nanoscale wells, for example, zero mode waveguides (ZMWs). In other embodiments, the array regions comprise nanopores.

Provision of the PEG and cation can facilitate loading of large nucleic acids into the array regions. Thus, in some embodiments, the nucleic acids (e.g., the templates of the polymerase-template complexes) are at least about 10 kb in length, at least about 20 kb in length, at least about 30 kb in length, or at least about 40 kb in length. Provision of the PEG and cation can also facilitate more rapid loading than can be achieved in the absence of these reagents. Thus, in some embodiments, distributing is complete in about 0.5-5, 1-4.5, 1.5-4, 1-3, or 2-3.5 hours.

In embodiments in which polymerase-template complexes are distributed into the array regions, the templates of the polymerase-template complexes are optionally hybridized to primers. The polymerase-template complexes can be immobilized in the array regions, for example, at the bottom of nanoscale wells, e.g., by binding to a moiety located at the bottom of each well.

The nucleic acids can diffuse through the solution, or their movement can be assisted, e.g., by beads to which the nucleic acids are attached. Thus, in one class of embodiments, the polymerase-template complexes are bound to magnetic beads, the array regions comprise nanoscale wells having bases having coupling agent bound thereto, and the methods include applying a dynamic magnetic field to move the magnetic beads in solution down to the top of the surface. The dynamic magnetic field also causes the beads to be moved across the surface, whereby some polymerase-nucleic acid complexes become bound to the coupling agent on the bases of the nanoscale wells. In another class of embodiments, the array regions comprise nanoscale wells comprising a coupling agent at their bases, and the polymerase-template complexes diffuse through the solution to the bases of the nanoscale wells and bind to the coupling agent, thereby immobilizing the polymerase-template complexes in the nanoscale wells.

In one class of embodiments, the templates in the polymerase-template complexes are of different lengths, at least one of which lengths is greater than 10 kb. After immobilization of the complexes in nanoscale wells, the percentage of nanoscale wells occupied by immobilized templates whose length is greater than 10 kb is equal to or greater than the percentage of templates in the initial solution whose length is greater than 10 kb. In a related class of embodiments, the templates in the polymerase-template complexes are of different lengths, at least one of which lengths is greater than 20 kb. After immobilization of the complexes in nanoscale wells, the percentage of nanoscale wells occupied by immobilized templates whose length is greater than 20 kb is equal to or greater than the percentage of templates in the initial solution whose length is greater than 20 kb. In one class of embodiments, the templates in the polymerase-template complexes comprise a first template whose length is at least 20 times the length of a second template. After immobilization of the complexes, a ratio of immobilized first template to immobilized second template is equal to or is greater than a ratio of first template to second template in the initial solution.

In some embodiments, after distribution and optional immobilization of the nucleic acids (e.g., polymerase-template complexes), at least 38% of the array regions are occupied by a single immobilized nucleic acid (e.g., a single immobilized polymerase-template complex), e.g., at least 50% or at least 75% of the regions. In one exemplary class of embodiments, polymerase-template complexes are distributed to and immobilized nanoscale wells, and after the immobilizing step at least 38% or at least 50% of the nanoscale wells are occupied by a single immobilized polymerase-template complex.

The nucleic acids can be, e.g., fully or partially double-stranded or single-stranded. Suitable nucleic acids include, but are not limited to, SMRTbells™ (circular nucleic acids having a double-stranded central region and single-stranded hairpin ends), double-stranded circular DNA molecules (e.g., nicked or gapped double-stranded circular DNA molecules, e.g., nicked or gapped plasmids), and linear molecules (e.g., genomic DNA fragments). In one exemplary class of embodiments, polymerase-template complexes are distributed to the array regions, and the templates of the polymerase-template complexes each comprise a double-stranded central region and two identical single-stranded hairpin end regions. Optionally, the double-stranded central region is at least about 5 kb in length, e.g., at least about 10 kb, at least about 20 kb, at least about 30 kb, or at least about 40 kb. In a related exemplary class of embodiments, the templates of the polymerase-template complexes each comprise a double-stranded central region and two different single-stranded hairpin end regions. In another exemplary class of embodiments, polymerase-template complexes are distributed to the array regions, and the templates of the polymerase-template complexes comprise nicked or gapped double-stranded circular DNA molecules. Optionally, the double-stranded circular DNA molecules are at least about 5 kb in length, e.g., at least about 10 kb, at least about 20 kb, at least about 30 kb, or at least about 40 kb. In another exemplary class of embodiments, polymerase-template complexes are distributed to the array regions, and the templates of the polymerase-template complexes comprise linear molecules, e.g., double-stranded molecules, e.g., genomic DNA fragments or amplicons. Optionally, the linear templates are at least about 5 kb in length, e.g., at least about 10 kb, at least about 20 kb, at least about 30 kb, or at least about 40 kb.

Loading of nucleic acids into array regions can facilitate subsequent analysis of the nucleic acids, for example, nucleic acid sequencing, and in particular single-molecule nucleic acid sequencing. Thus, the methods optionally include analyzing the nucleic acids in the array regions, e.g., by determining their nucleic acid sequence. The PEG is optionally removed from the nucleic acids, e.g., by washing, prior to such analysis.

Essentially all of the features noted for other embodiments herein apply to these embodiments as well, as relevant.

In some aspects, the invention provides methods for loading polymerase-nucleic acid complexes onto a substrate. In the methods, a solution of beads is provided, individual beads having bound thereto a plurality of polymerase-nucleic acid complexes. The solution is exposed to a substrate in the presence of at least one nucleic acid condensing agent. Preferably, the substrate comprises an array of zero mode waveguides. The substrate comprises coupling groups selective for coupling the polymerase-nucleic acid complexes to the substrate, e.g., within the zero mode waveguides. A field is applied to draw the beads to the substrate, whereby polymerase-nucleic acid complexes become bound to the substrate through the coupling groups.

Suitable nucleic acid condensing agents are described herein. In one class of embodiments, the at least one nucleic acid condensing agent comprises polyethylene glycol (PEG), e.g., PEG 8000. In one class of embodiments, the at least one nucleic acid condensing agent comprises a cation, e.g., a monovalent cation and/or a divalent cation. In a preferred class of embodiments, the at least one nucleic acid condensing agent comprises polyethylene glycol (PEG) and a cation (e.g., a monovalent cation), e.g., PEG 8000 and $K^+$, PEG 8000 and $Sr^{2+}$, or PEG 8000, $K^+$, and $Sr^{2+}$.

In some embodiments the field that draws the beads to the substrate is a magnetic, electric, or gravitational field. The methods can include applying a field that moves the beads across the surface of the substrate. In some embodiments, the field to draw the beads to the substrate and the field to move the beads across the substrate comprise different types of fields. In other embodiments, the field to draw the beads to the substrate and the field to move the beads comprise the same type of field, e.g., a magnetic field. In some embodiments the magnetic field is applied using one or more permanent magnets that are moved with respect to the substrate. In some embodiments the magnetic field is applied using one or more electromagnets.

In some embodiments, the methods include removing the beads from the substrate, leaving the bound polymerase-nucleic acid complexes on the substrate. In some embodiments, the substrate comprises an array of zero mode waveguides. In some embodiments, the beads have diameters that are greater than the than the smallest cross-sectional dimension of the zero mode waveguides. For example, the diameter of the beads can be two times greater or more than the smallest cross-sectional dimension of the zero mode waveguide. Optionally, the diameter of the beads is 2 times greater to 10,000 times greater than the smallest cross-sectional dimension of the zero mode waveguide. In one class of embodiments, the zero mode waveguides are cylindrical, and the smallest cross sectional dimensions are the diameters of the zero mode waveguides. In some embodiments, after applying the field, a portion of the zero mode waveguides have a single polymerase-nucleic acid complex attached thereto.

Provision of a nucleic acid condensing agent can also facilitate attachment of the nucleic acids to the beads. Thus, in one class of embodiments, providing the solution of beads comprises exposing beads to polymerase-nucleic acid complexes in the presence of PEG and a cation.

Essentially all of the features noted above apply to these embodiments as well, as relevant, e.g., with respect to solution composition, nucleic acid size, nucleic acid type, occupancy of the nanoscale wells by complexes, and the like.

In some aspects, the invention provides methods for loading active polymerase-nucleic acid complexes onto a substrate. In the methods, a solution of magnetic beads having polymerase-nucleic acid complexes bound thereto is provided. Each polymerase-nucleic acid complex comprises a polymerase enzyme and a template nucleic acid. In the presence of at least one nucleic acid condensing agent, the solution of magnetic beads is contacted with the top of a substrate comprising an array of nanoscale wells having bases, wherein the bases of the wells have coupling agent bound thereto. A dynamic magnetic field is applied to move the magnetic beads in solution down to the top of the substrate, whereby the dynamic magnetic field also causes the beads to be moved across the top surface of the substrate, whereby some polymerase-nucleic acid complexes become bound to the coupling groups on the bases of the nanoscale wells.

Suitable nucleic acid condensing agents are described herein. In one class of embodiments, the at least one nucleic acid condensing agent comprises polyethylene glycol (PEG), e.g., PEG 8000. In one class of embodiments, the at least one nucleic acid condensing agent comprises a cation, e.g., a monovalent cation and/or a divalent cation. In a preferred class of embodiments, the at least one nucleic acid condensing agent comprises polyethylene glycol (PEG) and a cation, e.g., a monovalent cation, e.g., PEG 8000 and $K^+$, PEG 8000 and $Sr^{2+}$, or PEG 8000, $K^+$, and $Sr^{2+}$.

In some embodiments the beads have diameters that are greater than the smallest cross-sectional dimension of the nanoscale wells. For example, the diameter of the beads can be two times greater or more than the smallest cross-sectional dimension of the nanoscale wells. Optionally, the diameter of the beads is 2 times greater to 10,000 times greater than the smallest cross-sectional dimension of the nanoscale wells. In one class of embodiments, the nanoscale wells are cylindrical, and the smallest cross sectional dimensions are the diameters of the nanoscale wells. In some embodiments, after applying the field, a portion of the nanoscale wells have a single polymerase-nucleic acid complex attached thereto.

In some embodiments the polymerase-nucleic acid complexes are bound to the magnetic bead via hybridization between an oligonucleotide attached to the magnetic bead and a sequence on the template nucleic acid. In one class of embodiments, each polymerase-nucleic acid complex comprises the polymerase enzyme, the template nucleic acid, and a primer. In some embodiments, the primer comprises a 5' retrieval sequence that is complementary to an oligonucleotide attached to the magnetic bead and a 3' priming sequence that is complementary to the template nucleic acid. The retrieval sequence and the priming sequence can be connected by a flexible, hydrophilic linker, e.g., a PEG linker. In some embodiments, the retrieval sequence comprises poly(dA) or poly(A), and the oligonucleotide attached to the magnetic bead comprises poly(dT) or poly(T).

In some embodiments the dynamic magnetic field is produced using one or more moving permanent magnets. In some embodiments the dynamic field is produced using one or more electromagnets. In some embodiments the coupling agent at the bases of the wells comprises biotin. In some embodiments the polymerase enzyme is attached to streptavidin, neutravidin, or avidin for binding to the coupling agent.

Essentially all of the features noted above apply to these embodiments as well, as relevant, e.g., with respect to solution composition, nucleic acid size, nucleic acid type, occupancy of the nanoscale wells by complexes, and the like.

In some aspects, the invention provides methods for loading active polymerase-nucleic acid complexes onto a substrate. In the methods, a solution of magnetic beads having polymerase-nucleic acid complexes bound thereto is provided. Each polymerase-nucleic acid complex comprises a polymerase enzyme and a template nucleic acid. The polymerase-nucleic acid complex is bound to the bead by hybridization of a capture oligonucleotide to a sequence on the template nucleic acid, wherein the capture oligonucleotide comprises a retrieval sequence that is complementary to an oligonucleotide attached to the magnetic bead, a capture sequence that is complementary to the template nucleic acid, and a flexible, hydrophilic linker that connects the retrieval sequence and the capture sequence, e.g., a PEG linker.

The solution of magnetic beads is contacted with the top of a substrate comprising an array of nanoscale wells having bases, wherein the bases of the wells have coupling agent bound thereto. Typically, the beads have diameters that are greater than the smallest cross-sectional dimension of the nanoscale wells. A dynamic magnetic field is applied to move the magnetic beads in solution down to the top of the substrate. The dynamic magnetic field also causes the beads to be moved across the top surface of the substrate, whereby some polymerase-nucleic acid complexes become bound to the coupling agent on the bases of the nanoscale wells.

In some embodiments, each polymerase-nucleic acid complex further comprises a primer hybridized to the template nucleic acid. In other embodiments, the capture sequence is at the 3' end of the capture oligonucleotide and serves as a priming sequence.

Essentially all of the features noted above apply to these embodiments as well, as relevant, e.g., with respect to solution composition, nucleic acid size, nucleic acid type, magnets, occupancy of the nanoscale wells by complexes, and the like.

BRIEF DESCRIPTION OF THE DRAWINGS

FIG. 6 schematically illustrates a method for depositing molecules of interest such as polymerase-nucleic acid complexes onto substrates such as zero mode waveguide arrays.

Figure 1:
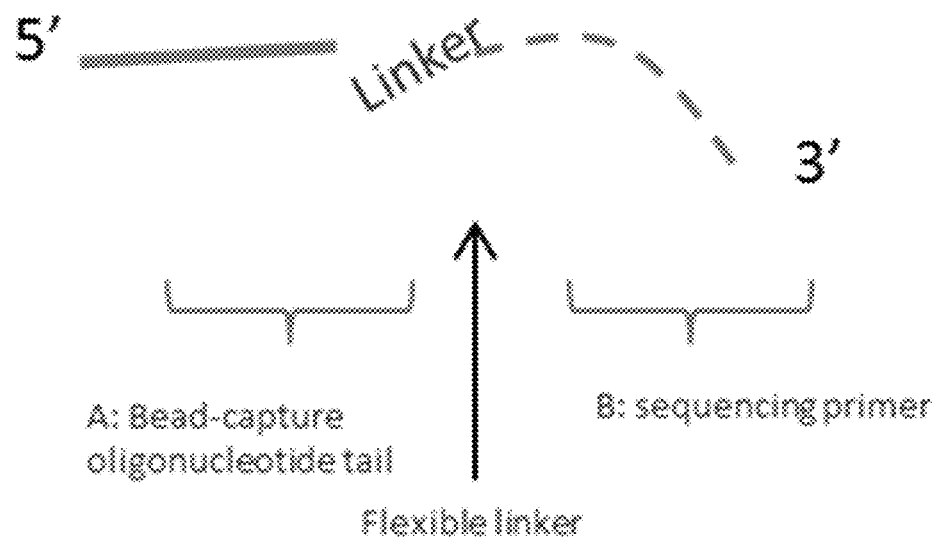
FIG. 1 schematically illustrates a primer including a bead-capture tail that can hybridize to an oligo-modified magnetic bead and a sequencing primer that can hybridize to a DNA template, separated by a flexible linker.

Schematic figures are not necessarily to scale.

DEFINITIONS

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Note that as used herein and in the appended claims, the singular forms "a," "an," and "the" include plural referents unless the context clearly dictates otherwise. Thus, for example, reference to "a protein" includes a plurality of proteins; reference to "a cell" includes mixtures of cells, and the like.

The term "about" as used herein indicates the value of a given quantity varies by +/−10% of the value, or optionally +/−5% of the value, or in some embodiments, by +/−1% of the value so described.

Where a range of values is provided, it is understood that each intervening value between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. A stated range generally includes one or both limits unless the context clearly dictates otherwise.

The term "nucleic acid" encompasses any physical string of monomer units that can be corresponded to a string of nucleotides, including a polymer of nucleotides (e.g., a typical DNA or RNA polymer), PNAs (peptide nucleic acids), modified oligonucleotides (e.g., oligonucleotides comprising nucleotides that are not typical to biological RNA or DNA, such as 2'-O-methylated oligonucleotides), and the like. A nucleic acid can be e.g., single-stranded or double-stranded. A nucleic acid of the present invention will generally contain phosphodiester bonds, although in some cases, nucleic acid analogs are included that may have alternate backbones, comprising, for example, phosphoramide, phosphorothioate, phosphorodithioate, or other backbones and linkages. The nucleic acid can have other modifications, such as the inclusion of heteroatoms, the attachment of labels, such as dyes, or substitution with functional groups, which will still allow for base pairing and for recognition of the nucleic acid by a polymerase enzyme where the nucleic acid is to be employed as a template.

An "oligonucleotide" is a polymer comprising two or more nucleotides. The polymer can additionally comprise non-nucleotide elements such as labels, quenchers, blocking groups, or the like. The nucleotides of the oligonucleotide can be deoxyribonucleotides, ribonucleotides or nucleotide analogs, can be natural or non-natural, and can be unsubstituted, unmodified, substituted or modified. The nucleotides can be linked by phosphodiester bonds, or by phosphorothioate linkages, methylphosphonate linkages, boranophosphate linkages, or the like.

A "kilobase" or "kb" is a unit used in designating the length of a nucleic acid sequence. 1 kb equals a sequence of 1000 bases or nucleotides. It will be evident that 1 kb can thus also represent a sequence of 1000 base pairs for a double-stranded nucleic acid.

A variety of additional terms are defined or otherwise characterized herein.

DETAILED DESCRIPTION

Among other aspects, the present invention provides methods, devices, compositions, and systems for distributing nucleic acid molecules (and any molecules or compounds associated with those nucleic acid molecules) into a plurality of array regions. Loading of nucleic acids onto substrates can facilitate subsequent analysis of the nucleic acids, for example, nucleic acid sequencing, and in particular single-molecule nucleic acid sequencing. Loading of nucleic acids, including polymerase-template complexes, into array regions such as zero mode waveguides (ZMWs), other nanoscale wells, or nanopores can be enhanced by the methods described herein. In one aspect, a nucleic acid condensing agent facilitates loading.

Introduction of a DNA condensation agent to the immobilization reaction media can facilitate loading, particularly of large nucleic acid templates into deep, narrow nanoscale wells. Without limitation to any particular mechanism, DNA is a molecule with a large radius of gyration, and its immobilization inside a nanostructure such as a ZMW is hindered by the slow diffusion rate of the DNA into the nanostructure. Again without limitation to any particular mechanism, provision of a condensation agent can facilitate DNA packing to itself and reduce its radius of gyration during immobilization, and consequently increase diffusion and overall immobilization speed and efficiency. The amount of sample required in order to achieve the desired degree of loading can also be reduced. Condensation agents can similarly decrease the radius of gyration and improve loading of other large nucleic acid molecules, e.g., RNAs.

In general, a nucleic acid condensing agent is a substance that, when added at an appropriate concentration to a solution containing a nucleic acid, compacts the nucleic acid. Typically, the nucleic acid condensing agent changes the shape of the nucleic acid from a random coil to a compacted toroid, sphere, or globule. Typically, such compaction reduces the contour size of the nucleic acid by at least 90%, more typically by at least 95%, or by at least 99% (e.g., the length of the extended chain compared to the diameter of the compacted toroid or sphere). The diameter of the compacted form can be, e.g., less than 200 nm, more typically less than 150 nm, less than 125 nm, or less than 100 nm. For example, DNA with an extended length of 1-100 μm can be compacted in the presence of a condensing agent to a sphere or toroid of about 100 nm. Condensation is reversible upon removal (or sufficient dilution) of the condensing agent.

Suitable nucleic acid condensing agents include, e.g., monovalent cations (e.g., $Na^+$, $K^+$, $Li^+$, $Rb^+$, and $Cs^+$), divalent cations (e.g., $Sr^{2+}$, $Mg^{2+}$, $Ca^{2+}$, $Zn^{2+}$, $Co^{2+}$, $Ni^{2+}$, $Eu^{2+}$, $Ba^{2+}$, and $Fe^{2+}$), trivalent cations (e.g., $Co^{3+}$), multi-positively-charged organic molecules and polymers (e.g., polyamines such as polylysine, spermidine or spermine, and other polycations), cationic transition metal complexes (e.g., hexamine cobalt), cationic surfactants, cationic lipids or liposomes, alcohols, wild-type and engineered DNA binding proteins (e.g., histones and bacterial histone-like proteins), nanoparticles, crowding agents (e.g., branched polysaccharides such as dextran), and polymers (particularly neutral or cationic hydrophilic polymers, particularly PEG polymers), as well as combinations thereof. For example, a combination of a hydrophilic polymer and a salt comprising a cation can be employed as the condensing agent.

In some embodiments, polyethylene glycols (PEGs, also known as polyethylene oxides) serve as the condensing agent. Exemplary PEGs include PEGs with an average molecular weight between about 200 and about 80,000, e.g., between about 200 and about 40,000, between about 200 and about 20,000, between about 600 and about 10,000, or between about 4000 and about 10,000. For example, the PEG can have an average molecular weight of about 400, about 600, about 1000, about 2000, about 4000, about 6000, about 8000, about 10,000, about 20,000, or about 40,000. The PEG can be polydisperse, having an average molecular weight as indicated, or the PEG can be monodisperse with all molecules having the same size. The PEG is typically a linear polymer, but can be a branched, star, or comb PEG (or a mixture of linear, branched, star, and/or comb types). Optionally, the terminal functional groups of the PEG are varied.

PEG can be provided at a final concentration in the immobilization mixture of about 2-30% weight/volume (w/v), e.g., about 2-20%, about 2-15%, or about 4-12% w/v. The concentration of PEG employed is typically inversely related to its molecular weight. As a few examples, where PEG 8000 (a linear PEG with an average molecular weight of 8000) is employed at a final concentration of about 8-14% or about 8-13% w/v, PEG 20,000 can be employed at a final concentration of about 6-10% w/v, or PEG 40,000 can be employed at a final concentration of about 4-7% w/v. In one class of embodiments, PEG 8000 is employed at a final concentration of about 2.5-25 mM (about 2-20% w/v), e.g., about 5-15 mM (about 4-12% w/v), about 10-15 mM (about 8-12% w/v), or greater than about 10.5 mM. In one exemplary embodiment, PEG 8000 is employed at a final concentration of about 4-12% w/v (i.e., at about 5-15 mM) in combination with a monovalent cation (e.g., $K^+$, $Na^+$, $Li^+$, $Rb^+$, or $Cs^+$) at a concentration between about 100 mM and about 300 mM (e.g., a concentration of about 250 mM). In another exemplary embodiment, PEG 8000 is employed at a final concentration of about 5-15 mM in combination with a divalent cation (e.g., $Sr^{2+}$, $Mg^{2+}$, $Ca^{2+}$, $Zn^{2+}$, $Co^{2+}$, $Ni^{2+}$, $Eu^{2+}$, $Ba^{2+}$, or $Fe^{2+}$) at a concentration between about 0.05 mM and about 10 mM, e.g., between about 1 and about 10 mM or between about 0.05 mM and about 0.3 mM (e.g., a concentration of about 0.15 mM). In another exemplary embodiment, PEG 8000 is employed at a final concentration of about 5-15 mM in combination with a monovalent cation (e.g., $K^+$ or $Na^+$) at a concentration between about 100 and about 300 mM (e.g., a concentration of about 250 mM) and a divalent cation (e.g., $Sr^{2+}$, $Mg^{2+}$, $Ca^{2+}$, $Zn^{2+}$, $Co^{2+}$, $Ni^{2+}$, $Eu^{2+}$, $Sn^{2+}$, $Ba^{2+}$, or $Fe^{2+}$) at a concentration between about 0.05 mM and about 0.3 mM (e.g., a concentration of about 0.15 mM).

Any of a variety of compositions similar to PEG can also be employed as a condensing agent. Suitable condensing agents thus include derivatives of PEGs, substituted PEGs (e.g., PEGs having pendant side chains), and modified forms of PEGs. Suitable condensing agents also include copolymers that include ethylene oxide/ethylene glycol subunits and/or substituted or modified forms thereof, e.g., block copolymers and random copolymers. In some embodiments, at least some of the subunits comprising such a copolymer are ethylene oxide/ethylene glycol subunits. In some embodiments, at least about 50% of the subunits comprising such a copolymer are ethylene oxide/ethylene glycol subunits, e.g., at least about 60%, at least about 70%, at least about 80%, at least about 90%, or at least about 95%. Exemplary useful polymers include, e.g., polyethylene glycol-polypropylene glycol copolymers and copolymers in which some subunits bear a side chain, e.g., a pendant amino group. See, e.g., PEG-A as described in Yoshikawa et al. (1997) J. Am. Chem. Soc. 119:6473-6477. Preferred copolymers are neutral or cationic. PEGs and PEG-containing compounds are collectively referred to herein as "PEG polymers" (or "polyethylene glycol polymers"). PEG-containing compounds include PEGs substituted with functional groups, PEGs having pendant side chains, and PEG copolymers. The size and/or concentration ranges noted above for PEGs apply to the other PEG polymers as well, as do the various configurations (linear, star, comb, branched, and the like).

Cations, including monovalent cations and divalent cations, can be provided as essentially any convenient salt, e.g., potassium acetate, potassium chloride, sodium chloride, strontium acetate, cobalt chloride, calcium chloride, zinc sulfate, or the like, as known in the art. A cation can be provided at a final concentration in the immobilization mixture between about 0.05 mM and about 1000 mM, e.g., between about 0.05 mM and about 500 mM, between about 50 mM and about 500 mM, between about 50 and about 400 mM, or between about 100 mM and about 300 mM. For example, a monovalent cation can be provided at a final concentration in the immobilization mixture between about 50 mM and about 500 mM, e.g., between about 50 mM and about 400 mM or between about 100 mM and about 300 mM. As another example, a divalent cation can be provided at a final concentration in the immobilization mixture between about 0.05 and about 10 mM, for example, between about 1 and about 10 mM where a monovalent cation is not also provided or between about 0.05 mM and about 0.3 mM where a monovalent cation is also provided.

In one class of embodiments, the nucleic acids and the condensing agent are applied to a substrate and the condensed nucleic acids diffuse to the desired locations. In one class of embodiments, the condensing agent serves to increase the density of a spike solution. In these embodiments, the higher density spike solution is applied to a liquid-covered substrate and sinks, carrying the nucleic acids with it to the array regions. In one class of embodiments, the nucleic acids are attached to beads. Optionally, motion of the beads in an applied field positions the condensed nucleic acids for localization on the substrate.

Inclusion of a condensing agent can be particularly beneficial for loading of larger templates. Thus, the nucleic acids to be loaded are optionally at least 5 kb in length, e.g., at least 10 kb, at least 15 kb, at least 20 kb, at least 25 kb, at least 30 kb, at least 40 kb, at least 50 kb, at least 70 kb, at least 100 kb, at least 200 kb, at least 500 kb, or even at least 1000 kb in length. The nucleic acids can be fully or partially double-stranded or can be single-stranded. Suitable nucleic acids include, but are not limited to, SMRTbells™ (circular nucleic acids having a double-stranded central region and single-stranded hairpin ends), double-stranded circular DNA molecules (e.g., nicked or gapped double-stranded circular DNA molecules, e.g., nicked or gapped plasmids), and linear molecules (e.g., genomic DNA fragments).

Inclusion of a condensing agent can facilitate loading of small amounts of nucleic acids. Thus, optionally, 1 picomole or less of nucleic acid can be applied to the substrate while still achieving the desired degree of loading. For example, 100 femtomoles or less, 10 femtomoles or less, 1 femtomole or less, or even 0.1 femtomoles or less of nucleic acid can be applied to the substrate. Similarly, optionally, 10 micrograms or less of nucleic acid can be applied to the substrate while still achieving the desired degree of loading. For example, 1 microgram or less, 100 nanograms or less, 50 nanograms or less, 10 nanograms or less, 5 nanograms or less, or even 1 nanogram or less of nucleic acid can be applied to the substrate. After distribution of the nucleic acids onto the substrate and optionally immobilization of nucleic acid molecules in or at the array regions, optionally at least 20% of the array regions are occupied by a nucleic acid molecule, e.g., at least 30%, at least 38%, at least 50%, or at least 67% of the array regions. In some embodiments, at least about 1% of the nucleic acids initially present in the sample occupy array regions after distribution of the nucleic acids onto the substrate and optionally immobilization of nucleic acid molecules in or at the array regions, e.g., at least about 2%, at least about 5%, or at least about 10%.

The condensing agent can be removed (e.g., by washing the array) after distribution of the nucleic acids onto the substrate and optional immobilization of nucleic acid molecules in or at the array regions, permitting the nucleic acids to uncondense. As another example, the concentration of the condensing agent can be reduced (e.g., by diluting the solution) to permit the nucleic acids to uncondense. In embodiments in which analysis is subsequently performed on the nucleic acids (e.g., single molecule sequencing), for preferred condensing agents, either the agent can be completely removed or the agent (or, in embodiments in which the agent is removed, any residual agent) does not interfere with the analysis. For embodiments in which protein-nucleic acid complexes are loaded, preferred condensing agents do not deleteriously affect a relevant activity of the protein (e.g., nucleic acid binding, enzymatic activity, or the like).

For ease of discussion, the loading methods described herein will often refer to arrays of nanoscale wells (e.g., regular or irregular arrays). Such nanoscale wells can in certain examples be zero mode waveguides (ZMWs), and in further examples, those ZMWs may have biotinylated bases and passivated sides, which can be of use in the methods of loading described herein as well as in later downstream applications, such as sequencing reactions. As will be appreciated, any discussion herein referring to nanoscale wells and/or ZMWs is applicable to any form of reaction sites and encompasses all types of surfaces, shapes and configurations of regions into which molecules of interest can be loaded. Similarly, for ease of discussion, the loading methods described herein will often refer to PEG and cations as useful for condensing for nucleic acids. As will be appreciated, any discussion herein referring to PEG and/or cations is applicable to any form of nucleic acid condensing agent and encompasses all types of compositions that condense nucleic acids, thereby facilitating their loading into reaction sites. For ease of discussion, the loading methods described herein will often refer to polymerase-template complexes (also referred to as polymerase-nucleic acid complexes). As will be appreciated, any discussion herein referring to loading of polymerase-template complexes is applicable to loading of any form of nucleic acid, including isolated nucleic acids or complexes of nucleic acids with other components.

Compositions produced by, or of use in, the methods of the invention are also features of the invention, as are related kits and systems.

Bead-Assisted Loading

Useful techniques for loading nucleic acids onto a substrate are detailed in U.S. Pat. No. 8,715,930, which is hereby incorporated by reference in its entirety for all purposes. Generally, the nucleic acids (including, e.g., polymerase-nucleic acid template complexes) are attached to beads, e.g., magnetic beads. A field is provided to bring the beads into proximity or contact with the substrate and optionally to move the beads with respect to the substrate. The nucleic acids or nucleic acid complexes become bound to the substrate, for example, through coupling groups on the substrate. In some embodiments, the substrate comprises an array of nanoscale wells such as zero mode waveguides (ZMWs). In further embodiments, the nucleic acids or complexes become bound to the base of the wells.

Loading of nucleic acids, including polymerase-template complexes, can be enhanced by the methods described herein. In one aspect, a flexible linker is incorporated into an oligonucleotide that captures the template nucleic acid to the bead. In another aspect, at least one nucleic acid condensing agent is included in the solution in which the bead-bound nucleic acids are contacted with the substrate. It will be evident that the various techniques described herein can be employed separately or in combination, with each other and/or with the techniques described in U.S. Pat. No. 8,715,930.

Oligonucleotides Including Flexible Linkers

In one general class of embodiments, nucleic acids of interest (e.g., templates) are captured to beads by hybridization with an oligonucleotide. In exemplary embodiments, the oligonucleotide is attached to a bead and is complementary to the nucleic acid. In some embodiments, the oligonucleotide is attached directly to the bead, while in other embodiments the oligonucleotide is indirectly bound to the bead. For example, in one class of embodiments, the oligonucleotide is complementary to the nucleic acid of interest and to another oligonucleotide that is in turn attached to the bead. For applications in which the nucleic acid is to be sequenced after it is immobilized on the substrate, the oligonucleotide optionally serves as a sequencing primer.

Figure 2A:
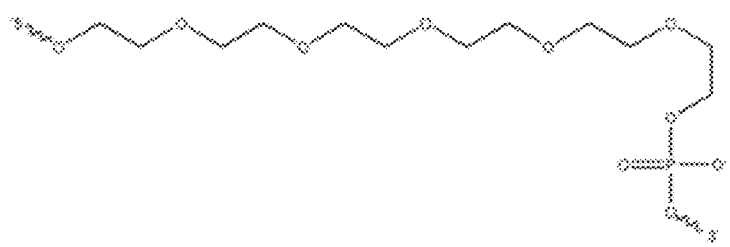
FIG. 2A illustrates an exemplary flexible linker that contains a six unit PEG spacer.

One example provides a novel primer design. As schematically illustrated in FIG. 1, the primer has three parts: A: a bead-capture tail that hybridizes to an oligo-modified magnetic bead; B: a sequencing primer that hybridizes to DNA template; and C: a flexible linker (e.g., a polyethylene glycol (PEG) linker) that separates and connects A and B, potentially reducing steric interference of the two hybridization events. An exemplary PEG linker is shown in FIG. 2A.

Figure 2B:
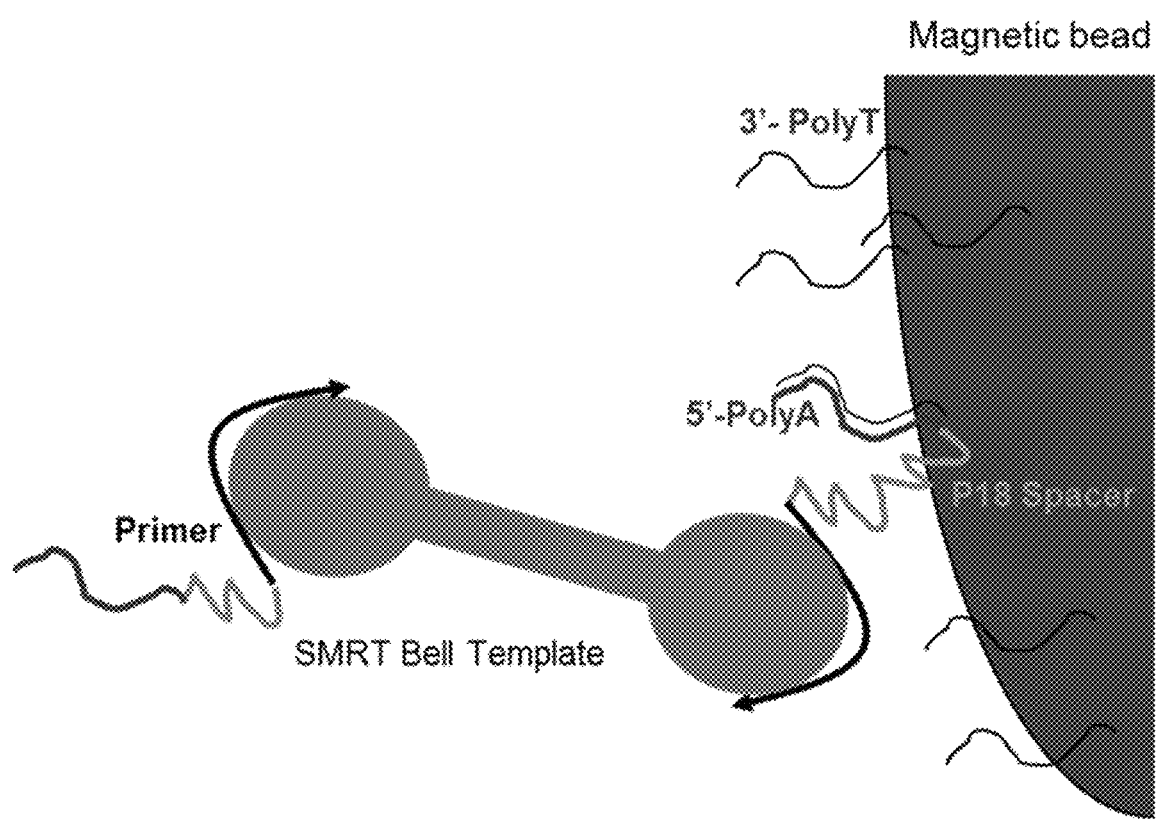
FIG. 2B schematically illustrates capture of a symmetric SMRTbell™ template to magnetic beads using a primer as in FIG. 1. Polymerase molecules that would bind to the SMRTbell™-primer complexes are not shown in this figure.

As schematically illustrated in FIG. 2B, during DNA immobilization, the 3' side of the linker containing—primer is typically first hybridized to template (e.g., a SMRTbell™, which has a double-stranded central region and two single-stranded hairpin end regions), then the primer-template complex is captured to magnetic beads (e.g., poly-T coated beads) by hybridization with the 5' side of the primer (e.g., a poly-A tail). Without limitation to any particular mechanism, it is thought that if no spacer is present between the two hybridization sequences, both hybridization events happen at the surface of the bead, which is densely covered by poly-T oligonucleotides. Due to steric hindrance at the surface of the beads, the polyA-to-polyT hybridization in particular is thought to be incomplete, giving fewer than the expected number of A:T base pairs and less stability. This is thought to potentially result in inefficient capture of SMRTbell™ as well as loss of the SMRTbell™ from the bead after the initial capture, which can in turn compromise DNA immobilization to nanostructures such as ZMWs. Inclusion of the flexible linker can thus decrease steric hindrance between the template and beads and increase immobilization efficiency, e.g., by providing additional distance between the template and bead and providing increased flexibility.

In one class of embodiments, the flexible linker comprises a PEG linker. The PEG spacer is flexible, hydrophilic, and does not exhibit non-specific binding interaction with polymerases. The PEG spacer optionally includes 2-30 PEG units, e.g., 4-20 units, 6 units (18 atoms), or 12 units (36 atoms). Other flexible hydrophilic moieties can also be employed. Linkers that do not increase nonspecific binding interactions, e.g., with polymerase, are preferred. Non-nucleotide spacers are therefore preferred, since merely including extra bases between the capture and priming regions of the oligonucleotide can increase nonspecific polymerase binding and/or may not relieve steric hindrance as efficiently.

In the example illustrated in FIG. 2B, the SMRTbell™ template is symmetric (it includes a double-stranded central region and two identical single-stranded hairpin end regions). One copy of the primer can therefore bind to each of the single-stranded end regions. In other embodiments, an asymmetric SMRTbell™ template is employed (including a double-stranded central region and two single-stranded hairpin end regions having different sequences). In such embodiments, a capture oligonucleotide including a flexible hydrophilic linker can be hybridized to one end region for capture of the template to a bead, while a separate sequencing primer is hybridized to the other end region.

It will be evident that oligonucleotides used to capture the nucleic acids to beads can be bound directly to the beads or can be indirectly bound to the beads (e.g., through hybridization to another oligonucleotide that is in turn bound to the beads, e.g., through polyA-polyT hybridization).

Nucleic Acid Condensation Agents

As described above, introduction of a nucleic acid condensation agent to the immobilization reaction media can facilitate loading, particularly of large nucleic acid templates (e.g., greater than 10 kb, greater than 15 kb, greater than 20 kb, greater than 30 kb, greater than 40 kb, greater than 50 kb, greater than 70 kb, greater than 100 kb, greater than 200 kb, greater than 500 kb, or even greater than 1000 kb) into deep, narrow nanoscale wells. Without limitation to any particular mechanism, even when beads are employed to facilitate loading, the large radius of gyration of DNA templates can hinder their immobilization inside a nanostructure such as a ZMW. Again without limitation to any particular mechanism, provision of a condensation agent can facilitate DNA packing to itself and reduce its radius of gyration during immobilization, and consequently increase immobilization speed and efficiency.

Suitable condensing agents have been described above, and include monovalent cations (e.g., $Na^+$ and $K^+$), divalent cations (e.g., $Sr^{2+}$, $Mg^{2+}$, $Ca^{2+}$, $Zn^{2+}$, $Ni^{2+}$, $Eu^{2+}$, $Ba^{2+}$, and $Fe^{2+}$), trivalent cations (e.g., $Co^{3+}$), multi-positively-charged organic molecules (e.g., spermidine, histones, and other polycations), nanoparticles, and polyethylene glycols (PEGs) and PEG polymers, as well as combinations thereof. In preferred embodiments, a combination of PEG and at least one cation is employed. Exemplary PEGs and cations have been detailed above, as have suitable concentration ranges.

In addition to increasing the number of ZMW wells productively loaded, inclusion of PEG also improves the uniformity of DNA immobilization. Without limitation to any particular mechanism, PEG efficiently prevents surface drying during immobilization and subsequent washing steps, and this reduces DNA loss and polymerase deactivation during such drying events. This also improves the overall immobilization performance.

It will be evident that various workflows can be employed to achieve the desired final concentration of nucleic acid condensation agent in the immobilization mixture. For example, for loading of polymerase-template complexes into ZMWs, the polymerase-template complexes can be formed and attached to beads in an aqueous solution lacking PEG, then applied to a ZMW chip covered with a layer of an equal volume of another aqueous solution containing PEG at twice the desired final concentration, such that after mixing on-chip the desired final concentration of PEG (and cations) is achieved. As another example, the polymerase-template complexes can be bound to beads, and PEG/cations can be added to the complexes before they are contacted with the ZMW chip. In yet another example, the nucleic acid condensing agent is present when the template (or other nucleic acid) is bound to the beads. Presence of PEG and cations, or another condensing agent, during binding of the nucleic acids to the beads can improve loading of the beads. For capture of SMRTbell™ templates through hybridization of poly-dA on the template (or on a capture primer as described above) to poly-T coated beads, binding efficiency generally decreases as the size of the DNA template increases. Capture of large templates (e.g., greater than 10 kb, greater than 15 kb, greater than 20 kb, greater than 30 kb, greater than 40 kb, greater than 50 kb, greater than 70 kb, greater than 100 kb, greater than 200 kb, greater than 500 kb, or even greater than 1000 kb) can thus be enhanced by inclusion of PEG and at least one cation (e.g., as detailed above for loading) during immobilization of the template onto the beads, optionally in addition to during loading of the bead-bound templates into ZMWs. Nucleic acids can also be captured to beads through nonspecific binding (e.g., electrostatic interactions) rather than through hybridization, in the presence of PEG and cation.

Physical Transfer of Isolated Polymerase-Nucleic Acid Complexes to Substrates

As detailed in U.S. Pat. No. 8,715,930, beads can be employed for deposition of isolated polymerase-nucleic acid complexes directly onto substrates. In general, the technique comprises obtaining a solution of beads that have polymerase-nucleic acid complexes attached to them. The solution of beads is brought into contact with or in close proximity to a substrate onto which it is desired to deposit the complexes (preferably in the presence of a nucleic acid condensing agent, as detailed above). The substrate that is used is prepared to have groups that bind to the polymerase-nucleic acid complexes. After the solution of beads is brought into contact with the surface, the beads are removed, leaving polymerase-nucleic acid complexes bound to the substrate. Prior to removal of the beads from the substrate, it is also generally desirable to induce movement between the beads and the substrate, e.g. moving the beads across the surface of the substrate in order to increase the number of complexes that are deposited. Prior to removal of the beads from the substrate, it can be desirable to induce dissociation of complexes from the beads, e.g., by adding an excess concentration of molecule(s) that weaken the magnitude of an affinity interaction between the beads and complexes. For example, in the case of templates with poly-dA sequence captured onto poly-T coated beads, a high concentration of single-stranded poly-A oligo can be added to compete template-polymerase complexes off the beads.

FIG. 6 shows an embodiment of the invention for loading polymerase-nucleic acid complexes onto a substrate directly from beads. A substrate 610 is provided. The substrate will generally have coupling groups that will react with moieties on the polymerase-nucleic acid complexes to bind the complexes to the surface. In the embodiment of FIG. 6, the substrate comprises an array of nanoscale wells or zero mode waveguides 616. The zero mode waveguides 616 on substrate 610 are nanoscale apertures through a cladding layer 614 that has been deposited onto a transparent substrate 612. The thickness of the cladding layer is generally from about 10 nm to about 300 nm. The zero mode waveguides can be, for example, cylindrical holes having diameters from about 10 nm to about 300 nm. Such zero mode waveguide arrays can be used for single molecule analysis such as single molecule sequencing as described herein. The zero mode waveguide can be in any suitable shape including cylinders or cones. The shape can be a channel. The cross sectional shape of the zero mode waveguide can be a circle, a triangle, a square, a rectangle, or an ellipse, or the cross sectional shape can be an arbitrary shape. For performing analysis within zero mode waveguides it is often desirable to have immobilized molecules of interest bound to the base of the zero mode waveguide, but to have little to substantially no molecules of interest on other parts of the substrate. Methods for treating the surfaces of zero mode waveguides including methods for obtaining selective coupling to the base of the zero mode waveguides are described, for example, in U.S. Pat. Nos. 7,833,398, 7,292,742 and in U.S. patent application Ser. No. 11/731,748, filed Mar. 29, 2007, Ser. No. 12/079,922, filed Mar. 27, 2008, and Ser. No. 12/074,716, filed Mar. 5, 2008, the full disclosures of which are incorporated by reference herein for all purposes. In some cases, for example, biotin is selectively coupled to the base of the zero mode waveguide.

Onto the substrate is dispensed a solution of beads 602 having molecules of interest, e.g. polymerase-nucleic acid complexes 604, bound to them. The complexes will generally have a binding moiety that will attach to the coupling group deposited onto the substrate surface. For example, where the substrate comprises biotin coupling groups, a biotin binding protein can be bound to the polymerase-nucleic acid complex. The biotin binding protein can be, for example, streptavidin that is bound to the polymerase enzyme. These polymerase-nucleic acid complex coated beads can be made in any suitable manner. The solution comprising the beads 602 is generally an aqueous solution having the components required for keeping the polymerase-nucleic acid complex together. The beads 602 can be magnetic beads. The size of the beads will depend on the application. In some cases, it is desirable that the beads have a diameter that is larger than the diameter of the zero mode waveguide.

In step (I), the beads are brought into contact with the substrate. This can be accomplished, for example, by applying a field that causes the beads to move down onto the top of the substrate. Where the beads are magnetic, a magnetic field can be used to draw the beads down. In addition to drawing the beads down, it can be desirable to provide a dynamic field that causes the beads to move across the top of the substrate. This can be accomplished, for example, by moving a permanent magnet under the substrate in a manner that causes the beads to move. One or more permanent magnets can be moved in a rotary fashion such that the beads are swept across the surface. In other cases, one or more fixed electromagnets provided with varying currents can be used to produce the dynamic field. In general, beads are referred to as magnetic beads where a magnetic field can be used to move the beads.

In step (II) the beads are removed from the substrate surface. Where magnetic beads are used, this removal or isolation can be performed by using magnets to the side and from above the sample.

The attachment between the polymerase-nucleic acid complex and the bead is broken during the process, leaving the complex bound to the surface while the beads are removed. There can be several places where the break in the attachment of the complex to the bead can occur. The place at which the break occurs can be controlled by designing into the construct linkages having appropriate levels of binding. Various types of linkages are possible, and some types have stronger binding than others. In some embodiments of the invention, a nucleic acid hybridization is used as the weakest link in the chain of binding. In some cases two or more hybridization linkages can occur in the chain of binding, and one can be made to be stronger than another, for example by having a longer region of sequence homology. The strength of the linkage can also be controlled by including modified or non-natural bases, e.g. peptide nucleic acids (PNAs), adding mismatched bases, and by changing the conditions in the solution including ionic strength and/or the temperature.

One example of controlling the position of the break in the linkage between the bead and the complex is provided where the polymerase enzyme is bound to the surface via a biotin-streptavidin linkage, the polymerase enzyme is bound to the nucleic acid by an enzyme-substrate interaction at the active site, the nucleic acid is bound to a hook oligonucleotide by hybridization with a capture sequence on the hook oligonucleotide to a sequence on a hairpin adaptor portion of the nucleic acid of about 10 to about 15 base pairs, and the hook oligonucleotide is attached by hybridization from a retrieval region on the hook oligonucleotide of about 18 to about 30 nucleotides to an oligonucleotide attached to a magnetic bead, e.g. with a poly(dA) region on the hook oligonucleotide and a poly(dT) region on the magnetic bead.

For this type of construct, the hybridization linkage between the capture region of the hook and the nucleic acid is the weakest link that is most susceptible to breaking during the magnetic bead loading. Having breakage at this locus is advantageous, as it leaves the polymerase-nucleic acid complex on the surface without the hook or any portion of the bead attached to it.

The beads coated with polymerase-nucleic acid complex can be produced as described herein or in any other suitable manner. While the invention is described in terms of beads, it is to be understood that other solid surfaces having polymerase-nucleic complexes attached can be used, as long as the solid surface can be brought into proximity or into contact with the substrate to deposit polymerase-nucleic acid complexes. The beads are generally spherical, but can have any other suitable shape, for example fibers, rods, disks, cubes, or other shaped materials can be used. Beads are useful as they can be readily manipulated within a solution. Beads for use in the invention can be functionalized on their outer surfaces for the attachment of polymerase-nucleic acid complexes. Suitable beads include polymeric beads having functional organic molecules on their surfaces allowing for such attachment. A variety of types of types of beads are known and used and many are commercially available. The beads can be produced in various size ranges from the nanometer to the millimeter size range. In some cases, the beads can be produced to be relatively monodisperse, which can be helpful in obtaining consistent results.

The beads can be brought into proximity or contact with the substrate in a variety of ways. Forces such as gravitational force, centrifugal force, magnetic, electrical, or dielectric forces or a combination thereof can be used to bring the beads into contact with the surface and to move the beads with respect to the surface. In preferred approaches, magnetic beads are used, and magnetic fields are applied both to bring the beads down into proximity or into contact with the substrate and to move the beads across the substrate.

Magnetic beads have been used for purification and separation in chemical and biochemical processes, and functionalized magnetic beads are commercially available. For example, NEB offers a variety of magnetic beads including Amylose Magnetic Beads, Anti-MBP Magnetic Beads, Chitin Magnetic Beads, Goat Anti-Mouse IgG Magnetic Beads, Goat Anti-Rabbit IgG Magnetic Beads, Goat Anti-Rat IgG Magnetic Beads, Hydrophilic Streptavidin Magnetic Beads, Protein A Magnetic Beads, Protein G Magnetic Beads, Streptavidin Magnetic Beads, SNAP-Capture Magnetic Beads, Oligo(dT) Magnetic Beads; Dynal (Life Technologies) offers a variety of functionalized magnetic beads including streptavidin coated beads, beads for binding with His tags, anion exchange, cation exchange, hydrophobic capture, and antibody beads. Micromod offers magnetic beads functionalized with surface functionalities NH2, PEG-NH2 and PEG-COOH for the covalent binding of proteins, antibodies or other molecules. Tubobeads LLC offers beads having streptavidin, sulfonate, carboxylate, or ammonium functionality. Spherotech Inc. offers magnetic beads having a variety of functionalities including carboxyl, amino, antibodies, and proteins. Using functionalized beads and known methods of surface polymer synthesis, beads with a variety of properties can be made, including those having oligonucleotides or peptides having specified sequences.

The beads can comprise polymers including polystyrene/polymethacrylate, dextran, crosslinked dextran, silica-fortified dextran, starch (BNF-starch particles), poly(lactic acid), poly(ethylene imine), or chitosan. The beads can also be made from inorganic material such as carbon, iron oxide, silica, or silicon. The magnetic beads can be useful as long as they are effectively moved by an applied magnetic field. For example, the beads can be ferromagnetic or paramagnetic, or superparamagnetic.

The methods, compositions, and devices of the invention are particularly useful for performing single-molecule analysis. A reason for this is that the methods are useful for providing molecules of interest such as polymerase-nucleic acid complexes at relatively sparse levels on a substrate. Thus the method can be used to deposit molecules of interest on a substrate such that the molecules of interest are provided at a surface density such that the molecules of interest are independently optically observable. In some cases, the substrate comprises an array of nanoscale wells such as arrays of zero mode waveguides (ZMWs). For example, the substrate can have a transparent lower layer comprised, for example, of fused silica, upon which is deposited a cladding layer with a thickness of between about 10 nm and about 500 nm. The cladding layer is generally an opaque layer and can be a metal layer. Through the cladding layer is an array of holes extending to the transparent substrate, and in some cases extending into the transparent substrate. The holes can have any suitable cross-sectional profile including a circular profile. Where the holes have a circular profile, the diameter of the holes is generally from about 20 nm to about 500 nm. The holes extending to the transparent substrate will generally have a portion of the transparent substrate as their base, thus forming nanoscale wells. For use in the present invention, the arrays of nanoscale wells are functionalized such that binding molecules are attached at the bases of the wells for binding the molecule or molecules of interest, such as a polymerase-nucleic acid complex, within the well. In some cases, the arrays are selectively functionalized such that a higher density of binding molecules is present within the wells than outside of the wells. Approaches to functionalizing zero mode waveguide substrates are provided in U.S. Pat. Nos. 7,833,398, 7,292,742 and in U.S. patent application Ser. No. 11/731,748, filed Mar. 29, 2007, Ser. No. 12/079,922, filed Mar. 27, 2008, and Ser. No. 12/074,716, filed Mar. 5, 2008, the full disclosures of which are incorporated by reference herein for all purposes. As described elsewhere herein, these nanoscale wells provide for carrying out analyses on very small numbers of molecules down to single molecules. In some cases the methods, devices, and compositions of the invention allow for the deposition of single molecules of interest within nanoscale wells.

When depositing molecules of interest, e.g. polymerase-nucleic acid complexes into ZMWs, in some cases, it is desirable for the diameter of the beads to be larger than the smallest cross-sectional dimension for the ZMW; where the ZMW has a circular profile, larger than the diameter of the ZMW. In some cases the diameter of the bead is 20% greater or more than the smallest cross-sectional dimension of the ZMW. In some cases the diameter of the bead is 2 times greater or more than the smallest cross-sectional dimension of the ZMW. In some cases the diameter of the bead is 2 times greater to 10,000 times greater than the smallest cross-sectional dimension of the ZMW. In other cases, it can be useful to have the size of the bead be smaller than the size of the ZMW. The size of the beads can be, for example, from about 40 nm to about 10 microns in diameter.

As would be understood in the art, the beads generally do not have a perfectly spherical shape, and are generally not perfectly monodisperse, but will have a distribution of sizes and shapes. In addition, where the outsides surfaces of the particles are composed of polymers that are soluble or partly soluble in the solution, the surfaces are not smooth flat surfaces, but the groups attached to the surface can extend from the bead on polymer chains into the solution. Though not bound by theory, it is believed that in some cases these polymer chains extending into solution can provide polymer-nucleic acid complex into nanoscale wells from beads that would be too large to fit into the wells. This property can be used to advantage in the loading of ZMWs. In some cases, spacer or linker molecules are provided on the bead surface between a functional group on the bead and the group that is used to link to the hook molecule or to link directly to the molecule of interest such as the polymerase-nucleic acid complex. By varying the length of the spacer or linker, one can provide for more or less reach between the surface of the bead and the molecule of interest. The spacer or linker can be any suitable molecular structure. It can be made, for example from a polymer such as polypeptide, poly(vinyl alcohol), polyethylene glycol, or polysaccharide. The linker will generally be made using a polymer that is soluble in the solution that the bead deposition takes place in. Where the molecule of interest is an enzyme, this is generally a polar solution, such as an aqueous environment, for which a polar or hydrophilic linker or spacer is used.

In some aspects, the invention provides a method for loading active polymerase-nucleic acid complexes onto a substrate comprising: providing a solution of magnetic beads having polymerase-nucleic acid complexes bound thereto, each polymerase-nucleic acid complex comprising a polymerase enzyme and a template nucleic acid; in the presence of at least one nucleic acid condensing agent, contacting the solution of magnetic beads with the top of a substrate comprising an array of nanoscale wells having bases, wherein the bases of the wells have coupling agent bound thereto; and applying a dynamic magnetic field from below the substrate to move the magnetic beads in solution down to the top of the substrate, whereby the dynamic magnetic field causes the beads to be moved across the top surface of the substrate, whereby some polymerase-nucleic acid complexes become bound to the coupling groups on the bases of the nanoscale wells. In some cases, the magnetic field is applied from above or adjacent to the substrate. For example, field focusing can be used which allows for applying magnetic fields from above, yet obtaining a field in which the field gradient is highest below the substrate, tending to pull the magnetic beads down.

The coupling groups or binding molecules on the substrate for coupling to the molecule of interest, e.g. polymerase-nucleic acid complex, can be any suitable coupling group or binding molecules. The coupling can be accomplished by forming a covalent bond or through a non-covalent interaction. It is generally desired that the coupling to the substrate result in a strong bond relative to the other linkages, e.g. between the polymerase-nucleic acid complex and the capture molecule and between the capture molecule and the bead. Many types of binding pairs are known in the art. In some cases, an interaction between biotin and a biotin binding protein such as avidin or streptavidin is used. In some cases, an antibody-antigen interaction, for example between digoxigenin and anti-digoxigenin, is used. Reactions that form covalent linkages, for example, Spy, SNAP, or Click chemistry, can be used to bind the polymerase-nucleic acid complex to the substrate. Oligonucleotide hybridization can also be used for the attachment. Where such hybridization is used, the linkages are designed such that the oligonucleotide binding to the surface is stronger, e.g. has a higher Tm, than the other linkages between the surface and the bead.

Binding of the polymerase-nucleic acid complex to the substrate is generally carried out by forming a bond to the polymerase. One member of the binding pair that is generally used to attach the complex to the substrate is connected directly or indirectly to the polymerase. In some cases, a biotinylation sequence is included when producing the polymerase, and the protein is biotinylated and attached to streptavidin prior to formation of the complex. The polymerase-streptavidin is then ready for binding to a substrate that is prepared by having biotin groups on its surface. In other embodiments, the nucleic acid template complexed with the polymerase is attached to the substrate. See, e.g., the references hereinbelow.

Where the molecule of interest comprises a polymerase-nucleic acid complex, the solution that is used for deposition with beads is generally an aqueous solution. The components of the solution and the conditions are controlled as described above in order that the polymerase-nucleic acid complex remains intact. For example, the appropriate level of monovalent and divalent ions, the concentration of nucleotide, the pH, and the temperature are controlled. It is also generally desired that the polymerase not continue to perform nucleic acid synthesis during deposition, and strontium and calcium can be added in order to inhibit or reduce polymerization. A condensing agent is included as described above to facilitate immobilization.

There is generally a plurality of molecules of interest attached to a bead. For example, there can be from tens to millions or more of molecules attached to a bead. In some cases, the beads, or a subset of the beads will each only have one molecule of interest attached.

Where beads are used to selectively deliver molecules of interest to the substrate, the beads can be brought into contact with the substrate by applying a force to the beads which can involve placing the beads in a field which applies such a force. An effective process for binding the molecules of interest generally involves applying both a field that forces the beads down to the surface of the substrate and a field that moves the beads across the surface of the substrate. These two fields can be different fields, or can be two components of the same field. The fields can be, for example, gravitational, centrifugal, magnetic, electric, or dielectric.

Preferred embodiments of the invention utilize a magnetic field both to bring down the particles and to move the particles across the surface of the substrate, either in contact with or in proximity to the substrate. The magnetic field can be applied using one or more permanent magnets, or using one or more electromagnets. Each of these approaches has its benefits and drawbacks, and each can be employed to carry out the invention. In some cases, one, two, three, four or more permanent magnets are held below the substrate, and are continuously moved with respect to the substrate. In this manner, the beads are both pulled down to the substrate and are moved across the substrate surface. The movement of the magnet or magnets can be in any pattern that provides suitable movement of the beads. The beads can be moved around in the plane of the substrate, or can be moved such that they move away from and back toward the substrate as well. A circular movement of one or more magnets underneath the substrate has been found to be straightforward to implement and to provide the requisite movement. In some cases, the magnets can remain fixed and the substrate moved with respect to the magnets. In some cases, both the substrate and the magnet are moved.

The choice of the mode of magnetic movement will also depend on the size and shape of the substrate to which the beads are to be contacted or moved into proximity of. For example, the magnets can be made to trace wider circles to ensure that the beads come into contact with the outer regions of a larger surface. In some embodiments, two magnets held next to one another under the substrate are used, one having its north pole facing upward, and the other having its north pole facing downward. This pair of magnets is attached to a mechanism that rotates the pair underneath the substrate. The pair of magnets is rotated in the plane of the substrate below the substrate at about 10 to about 120 rpm. In some cases, rotation rates of 1 rpm to 600 rpm, 3 rpm to 120 rpm, or 6 rpm to 20 rpm are used. The beads are moved across the substrate typically for about 5 to about 20 minutes, but in some cases for about 1 minute to about 2 hours. A variety of permanent magnets are readily available commercially. For example, Dura Magnetics Inc. has available on their website (www (dot) duramag (dot) com/magnet-material (dot) html) various magnets including magnets having various magnetic strengths. The type and shape of the permanent magnet can be chosen for ease of implementation and to optimize loading. For example, button magnets, bar magnets, or sheet magnets can be employed.

One or more electromagnets can also be utilized to move the particles for deposition. For example one or more electromagnets can be mounted below the substrate, and the current to the electromagnet(s) can be varied in order to vary the strength of the magnetic field. By placing multiple electromagnets in a pattern, and controlling the current to each of the electromagnets, a moving magnetic field can be produced above the substrate which can both bring down the magnetic particles and move the particles across the substrate surface. The use of electromagnets has the advantage that a system for moving the beads can be constructed with no moving parts. The current flowing through the electromagnets will produce heat at the electromagnet. When using this approach, this heat generation should be taken into account. In some cases, when using electromagnets, heat-sinking, insulation, and/or active cooling is provided to control the temperature.

The magnetic strength, number of magnets, speed of movement, distance from substrate, and time of deposition can be varied to obtain the desired results. Even for very small magnetic beads, microscopy can be used to observe the behavior of the cloud of beads being moved by the magnetic field in real time. These observations can also be used to set the appropriate parameters for deposition.

Gravitational fields can be used for relatively large beads. As the beads become smaller, however, the ability of a gravitational force to move the beads down from solution becomes limited. In some cases, the chip can be slowly rotated while the beads move across the top of the surface. The rotation allows for the beads to move relative to the chip surface. In some cases, the chip is tilted while it is rotated to facilitate the movement of the beads across the surface. Centrifugal fields can also be applied to bring down the beads and also to move the beads across the surface of the substrate. For example, the substrates can be mounted within a centrifuge such that the substrate is at an angle with the centrifugal force vector, and the substrate can be rotated such that the beads move around across its surface.

Electric fields can be used to move the particles where the particles have the characteristics that they will move in an electric field. For example, particles having a net charge, or particles made of a polymer having a net charge surrounded by counterions of the opposite charge, will move in an electric field. As with the description above for the magnetic field, a dynamic electric field can be used to both move the particles to the substrate and to move the particles across the surface of the substrate. Typically electrodes will be placed in contact with the solution. The appropriate voltages are then applied to the electrodes as a function of time to produce the electric field. Particles can also be made to move according to the invention using dielectric field gradients and alternating currents. Acoustic fields (sonication) can be used to move the beads relative to the surface. Hydrodynamic forces, e.g. through creation of a vortex, can also be utilized.

Combinations of fields can also be used. For example a magnet can be used to pull down the beads and another force, such as ultrasonication, can be used to move them, or centrifugation can be used to pull down the beads and a separate force used to move them.

One object of the invention is providing molecules of interest such as polymerase-nucleic acid complexes to a substrate for single molecule analysis. For single molecule analysis it is generally desired that single molecules of interest are bound to a substrate at a density and pattern such that the optical signal from one molecule can be detected distinctly from signals from other molecules and from solution. That is, the molecules are deposited so as to be individually optically resolvable. One method that has been used for this purpose is to deposit molecules of interest from a solution that is diluted such that on average, an acceptable number of single molecules will be individually optically resolvable. If the concentration is too high, the density on the surface will be such that few, if any, single molecules will be resolvable. If the concentration is too low, this may also result in very few single molecules. The methods, devices and compositions of the present invention provide an alternative approach for obtaining high levels of optically resolvable single molecules on a substrate.

As described above, a preferred substrate for single-molecule analysis is a zero mode waveguide (ZMW) array. Here, the optical analysis is carried out only within the ZMWs on the surface. The invention provides useful methods for loading single molecules into a ZMW array. As with other substrates for single molecule analysis, loading molecules of interest onto ZMWs to obtain acceptable numbers of single molecules has often been carried out with a dilution method where solutions at various dilution levels are applied to the surface to obtain the optimal loading. The methods of the invention provide tools for controlling the way in which molecules of interest are loaded into ZMWs. Other suitable substrates include, e.g., arrays of nanopores.

When depositing a library of polymerase-nucleic acid complexes onto a substrate, for example a ZMW substrate, by diffusion from solution, there can be a relatively large number of smaller fragments deposited than of larger fragments. By depositing with beads, particularly in the presence of a condensing agent, there can be a much more even distribution of deposited polymerase-nucleic acid complexes by size, allowing for a better representation of the larger size fragments in the data in single molecule analysis. In some cases, bead loading also allows for preferential loading of larger size fragments over smaller size fragments.

Since ZMWs are wells with defined dimensions, the sizes, shapes, and extension (reach) of the beads can be used to control the manner in which molecules of interest are deposited. For example in some cases, beads are used that have a size that is smaller than a characteristic dimension of the ZMW, such that a bead fits into a ZMW, and has a reach such that only molecules of interest from a bead fitting into the ZMW will be deposited. In some cases, beads will be used that are smaller than the diameter of a ZMW, but larger than half of the diameter of the ZMW. In this way, only one bead will deposit into the ZMW, preventing the deposition of a second bead, ensuring that each ZMW will only receive molecules of interest from one bead. For example, for a ZMW array having ZMWs with diameters of 200 nm, beads having diameters from about 100 nm to about 190 nm are used. Another way of controlling the level of loading is by controlling the density of molecules of interest on the surfaces of the beads. For example, by using sparsely functionalized beads, only small numbers of molecules of interest will be deposited.

Exemplary Process for Attaching Complexes to Magnetic Beads and Loading onto a ZMW Chip A library is produced having a plurality of double stranded fragments, the various fragments having sequences from portions of an original DNA sample. The plurality of double stranded fragments can be produced, for example, by shearing or using restriction enzymes. The size distribution can be controlled, for example, to give relatively long fragments—e.g. 10 kb or greater, or relatively small fragments—e.g. 200-300 bases. Hairpin adaptors are ligated onto the ends of the double stranded fragments to produce circular template molecules having a central double-stranded portion and single-stranded hairpin loops at the ends (see SMRTbells™ from Pacific Biosciences®). The hairpin adaptors are primed with primers having a 3'-poly (A) region. The primers hybridize with the hairpin adaptor portion such that the complementary region of the primer hybridizes to the hairpin adaptor while the poly(A) portion remains unhybridized and single stranded. The solution of primed SMRTbell™ templates is exposed to phi-29 polymerase under conditions in which the polymerase-nucleic acid complex forms. This step is generally carried out with an excess of polymerase.

A solution of magnetic beads having attached poly(T) DNA (e.g. Dynal beads) is added to a tube (optionally in the presence of a condensing agent as detailed herein). The beads are brought to the side of the tube with a magnet and rinsed with buffer, e.g. once with high salt, and once with a buffer similar to that used for sequencing or with a buffer including a condensing agent. The polymerase-nucleic acid complex is then added to the beads at the appropriate level of dilution (e.g. 20 pM), and the beads are re-suspended into this solution. The beads are in contact with the solution to allow the poly(A) tails of the primers to hybridize to the poly(T) groups on the beads. The level of attachment of the complexes to the beads can be determined by fluorometric methods.

The magnetic beads with polymerase-nucleic acid complex attached are then washed one to three times with buffer or salt solution. The wash steps remove unattached complex, unwanted components, and uncomplexed enzyme. In the last step, the magnetic beads with complex are dispersed into a sequencing reaction mixture or other buffer. This solution can be stored for use, for example at 4° C., or can be dispensed directly onto a substrate in the presence of a condensing agent as detailed herein. The solution can be dispensed onto a ZMW chip having one or more permanent magnets below the chip, and the magnets moved with respect to the chip to move the beads across the surface. In some cases, no magnet is required and gravity is used to load the complexes onto the chip. The exposure to the chip can be, for example from 15 minutes to about 6 hours. The shorter times can provide higher throughput, while the longer times allow for the loading of lower concentrations of template, which can be useful where a minimal amount of sample is available. The beads and optionally the condensing agent can then be removed, leaving the polymerase-nucleic acid complexes immobilized on the substrate.

Diffusion Loading

In other embodiments, diffusion of nucleic acids through the loading solution achieves the desired speed and degree of loading. Diffusion loading of nucleic acids, particularly large nucleic acids, can be enhanced by provision of a nucleic acid condensation agent. Without limitation to any particular mechanism, for large nucleic acid molecules, the large radius of gyration ordinarily results in unacceptably slow and inefficient loading by diffusion, but provision of a condensation agent can reduce the radius of gyration and consequently increase diffusion and overall immobilization speed and efficiency to useful levels. The amount and/or concentration of input nucleic acids can also be reduced.

Suitable condensing agents have been described above, and include monovalent cations (e.g., $Na^+$ and $K^+$), divalent cations (e.g., $Sr^{2+}$, $Mg^{2+}$, $Ca^{2+}$, $Zn^{2+}$, $Co^{2+}$, $Ni^{2+}$, $Eu^{2+}$, $Ba^{2+}$, and $Fe^{2+}$), trivalent cations (e.g., $Co^{3+}$), multi-positively-charged organic molecules (e.g., spermidine, histones, and other polycations), nanoparticles, and polyethylene glycols (PEGs) and PEG polymers, as well as combinations thereof. In preferred embodiments, a combination of PEG and at least one cation is employed to condense the nucleic acids. Exemplary PEGs and cations have been detailed above, as have suitable concentration ranges.

In one class of embodiments, a solution comprising the nucleic acids to be loaded (e.g., polymerase-template complexes), PEG, and a cation is prepared. The solution is then applied to the surface of the desired substrate. The nucleic acids diffuse through the solution to the array regions. It will be evident that various workflows can be employed to achieve the desired final concentration of nucleic acid condensing agent in the immobilization mixture. Thus, in another class of embodiments, the nucleic acids to be loaded (e.g., polymerase-template complexes) in an aqueous solution lacking PEG are applied to a substrate surface covered with a layer of an equal volume of another aqueous solution containing PEG at twice the desired final concentration, such that after mixing on the surface the desired final concentration of PEG (and cations) is achieved. The nucleic acids diffuse through the solution to the array regions.

As detailed for the embodiments above, the solution that is used for deposition is generally an aqueous solution. Where a polymerase-nucleic acid complex is to be deposited, the components of the solution and the conditions are controlled as described above in order that the polymerase-nucleic acid complex remains intact. For example, the appropriate level of monovalent and divalent ions, the concentration of nucleotide, the pH, and the temperature are controlled. It is also generally desired that the polymerase not continue to perform nucleic acid synthesis during deposition, and strontium and calcium can be added in order to inhibit or reduce polymerization.

Suitable substrates are described herein and include arrays of reaction regions, for example, arrays of nanoscale wells such as ZMWs or arrays of nanopores. Arrays can be regular or irregular. As detailed above, one object of the invention is providing molecules of interest such as polymerase-nucleic acid complexes to a substrate for single molecule analysis. For single molecule analysis it is generally desired that single molecules of interest are bound to a substrate at a density and pattern such that the optical signal from one molecule can be detected distinctly from signals from other molecules and from solution. That is, the molecules are deposited so as to be individually optically resolvable. As described above, a preferred substrate for single-molecule analysis is a zero mode waveguide (ZMW) array. Here, the optical analysis is carried out within the ZMWs on the surface.

As for other embodiments described herein, the nucleic acids are optionally immobilized or bound to the substrate in the array regions. For example, a nucleic acid can be immobilized at the base of a nanoscale well (e.g., ZMW) or within, on, or in proximity to a nanopore. For example, a coupling agent can be provided at the base of the well (e.g., a chemical cross-linking agent or a binding moiety). Binding of the nucleic acid, or of a molecule bound to the nucleic acid (e.g., a polymerase or primer), to the coupling agent thus immobilizes the nucleic acid in the well. Suitable techniques for immobilization are well known in the art; see, e.g., the references noted elsewhere herein and US patent application publications 2008/0032301 and 2014/0094375. In one class of embodiments, the polymerase comprises a biotin tag, and the polymerase-template complex is immobilized through binding of the biotin tag to a biotin-binding protein (e.g., streptavidin, avidin, neutravidin, traptavidin, or the like) that is in turn bound to the base of a nanoscale well, e.g., a biotinylated base. In another class of embodiments, the polymerase is covalently linked to a moiety attached to the base of the well, e.g., through reaction with an immobilized reactive functional group or through reaction of a polymerase bearing a SpyTag with an immobilized SpyCatcher peptide (see, e.g., Fairhead et al. (2014) J. Am. Chem. Soc. 136: 12355-12363 for discussion of the SpyTag/SpyCatcher system). In other embodiments, the template nucleic acid or a primer is biotinylated and binds to a biotin-binding protein on the surface or is chemically cross-linked to the surface.

As for the embodiments described above, for example, the polymerase can have a member of a binding pair connected to it which can bind to the other member of the binding pair attached to the substrate. Many types of binding pairs are known in the art. In some cases, an interaction between biotin and a biotin binding protein such as avidin or streptavidin is used. In some cases, an antibody-antigen interaction, for example between digoxigenin and anti-digoxigenin, is used. Reactions that form covalent linkages, for example, Spy, SNAP, or Click chemistry can be used to bind the polymerase-nucleic acid complex to the substrate. Oligonucleotide hybridization can also be used for the attachment.

Typically the polymerase enzyme is attached directly to the substrate. In other embodiments, the nucleic acid template complexed with the polymerase is attached to the substrate. Certain embodiments of template immobilization are provided, e.g., in U.S. Pat. No. 8,481,264, which is incorporated herein by reference. One skilled in the art will appreciate that there are many ways of immobilizing nucleic acids and proteins, whether covalently or non-covalently, via a linker moiety, or tethering them to an immobilized moiety. These methods are well known in the field of solid phase synthesis and micro-arrays (Beier et al., Nucleic Acids Res. 27:1970-1-977 (1999)). Non-limiting exemplary binding moieties for attaching either nucleic acids or polymerases to a solid support include streptavidin or avidin/biotin linkages, carbamate linkages, ester linkages, amide, thiolester, (N)-functionalized thiourea, functionalized maleimide, amino, disulfide, amide, and hydrazone linkages, among others. Antibodies that specifically bind to one or more reaction components can also be employed as the binding moieties. In addition, a silyl moiety can be attached to a nucleic acid or polymerase and to a substrate such as glass using methods known in the art.

Inclusion of a condensing agent can be particularly beneficial for diffusion loading of larger templates. Thus, the nucleic acids to be loaded are optionally at least 5 kb in length, e.g., at least 10 kb, at least 15 kb, at least 20 kb, at least 25 kb, at least 30 kb, at least 40 kb, at least 50 kb, at least 70 kb, at least 100 kb, at least 200 kb, at least 500 kb, or even at least 1000 kb in length. The nucleic acids can be fully or partially double-stranded or can be single-stranded. Suitable nucleic acids include, but are not limited to, SMRTbells™ (circular nucleic acids having a double-stranded central region and single-stranded hairpin ends), double-stranded circular DNA molecules (e.g., nicked or gapped double-stranded circular DNA molecules, e.g., nicked or gapped plasmids), and linear molecules (e.g., genomic DNA fragments). As described in greater detail hereinbelow, condensation of a large nucleic acid can result in a condensed molecule that excludes enough volume to disfavor immobilization of a second nucleic acid in the same array region or nanoscale well. The nanoscale wells (e.g., ZMWs) optionally have a critical dimension of 50 nm-400 nm or 50 nm-300 nm, e.g., the diameter of the top opening of the well or the diameter of the base of the well.

In the absence of a nucleic acid condensing agent, loading of mixed populations of nucleic acids into nanoscale wells tends to favor loading of the smaller nucleic acids, which (without limitation to any particular mechanism) have a smaller radius of gyration than do large nucleic acids and which can thus gain access to size-restricted reaction regions more readily. Addition of a nucleic acid condensing agent can eliminate this size bias in loading and, in some instances, can even favor loading of large nucleic acids. For example, inclusion of a nucleic acid condensing agent can result in loading and immobilization of large nucleic acids (e.g., nucleic acids greater than 5 kb, greater than 10 kb, greater than 20 kb, greater than 30 kb, greater than 40 kb, greater than 50 kb, greater than 70 kb, greater than 100 kb, greater than 200 kb, greater than 500 kb, or even greater than 1000 kb in length) being as efficient as loading and immobilization of smaller nucleic acids (e.g., 1 or 2 kb). For example, nucleic acids of a given length (e.g., 5 kb, 10 kb, 20 kb, 30 kb, 40 kb, 50 kb, etc.) can be represented among the immobilized population at the same frequency—or at an even greater frequency—than the frequency at which nucleic acids of that length were represented in the starting sample. Frequency can be assessed, e.g., as a percentage of nanoscale wells occupied by molecules of that length, or as the percentage of molecules in the initial sample having the indicated length. A ratio of templates of different sizes can also be assessed.

In one exemplary class of embodiments in which polymerase-template complexes are loaded, the templates in the polymerase-template complexes are of different lengths. At least one of the lengths is greater than 10 kb. After loading and immobilization of the sample in nanoscale wells, the percentage of the nanoscale wells occupied by immobilized templates whose length is greater than 10 kb is equal to or greater than the percentage of templates in the initial solution whose length is greater than 10 kb. Optionally, the initial solution also includes at least one nucleic acid whose length is less than 10 kb (e.g., less than 5 kb, less than 2 kb, or less than 1 kb); after loading and immobilization, the percentage of the nanoscale wells occupied by immobilized templates whose length is less than 10 kb is equal to or less than the percentage of templates in the initial solution whose length is less than 10 kb. In a related class of embodiments, the templates in the polymerase-template complexes are of different lengths, at least one of which lengths is greater than 20 kb. After loading and immobilization of the sample in nanoscale wells, the percentage of nanoscale wells occupied by immobilized templates whose length is greater than 20 kb is equal to or greater than the percentage of templates in the initial solution whose length is greater than 20 kb. Optionally, the initial solution also includes at least one nucleic acid whose length is less than 20 kb (e.g., less than 10 kb, less than 5 kb, less than 2 kb, or less than 1 kb); after loading and immobilization, the percentage of the nanoscale wells occupied by immobilized templates whose length is less than 20 kb is equal to or less than the percentage of templates in the initial solution whose length is less than 20 kb. As one specific example, if nucleic acids greater than 20 kb in length make up 75% of a starting sample, after loading and immobilization of the sample in nanoscale wells, at least 75% of the occupied wells will be occupied by nucleic acids greater than 20 kb in length.

In one exemplary class of embodiments in which polymerase-template complexes are loaded, the templates in the polymerase-template complexes comprise a first template whose length is at least 20 times the length of a second template (e.g., at least 25 times, at least 30 times, at least 40 times, at least 50 times, or at least 100 times). After loading and immobilization of the sample, a ratio of immobilized first template to immobilized second template is equal to or is greater than a ratio of first template to second template in the initial solution. For example, where 1 fmole of 20 kb template and 1 fmole of 1 kb template are present in a starting sample, after loading and immobilization of the sample in nanoscale wells, the ratio of wells occupied by immobilized 20 kb template to wells occupied by immobilized 1 kb template will be at least 1:1 (e.g., 1.5:1, 2:1, or 3:1 or more). It will be evident that typical samples can include a large number of nucleic acids of many varying lengths; the above examples merely call out two representative lengths chosen to assess relative loading efficiency of the different lengths.

As for the embodiments described above, in addition to increasing the number of ZMW wells productively loaded, inclusion of PEG also improves the uniformity of DNA immobilization. Without limitation to any particular mechanism, PEG efficiently prevents surface drying during immobilization and subsequent washing steps, and this reduces DNA loss and polymerase deactivation during such drying events. This also improves the overall immobilization performance.

Density Loading

Another general class of embodiments provides methods that result in improved loading of the nucleic acids as compared to typical diffusion loading methods not including condensing agents. In this class of embodiments, the condensing agent serves to increase the density of a spike solution. In these embodiments, the higher density spike solution is applied to a liquid-covered substrate and sinks, carrying the nucleic acids with it to the array regions. For additional details, see U.S. patent application 62/257,152 filed Nov. 18, 2015 by Sassan Sheikholeslami et al. and U.S. patent application Ser. No. 15/354,803 filed of even date herewith by Sassan Sheikholeslami et al. and entitled "Methods and Compositions for Loading of Polymerase Complexes," each of which is hereby incorporated by reference in its entirety for all purposes.

Methods, devices, compositions, and systems for distributing nucleic acid molecules (and any molecules or compounds associated with those nucleic acid molecules) into a plurality of array regions are provided. In general, the methods, devices, compositions, and systems result in improved loading of nucleic acids as compared to typical diffusion loading methods in the absence of a condensing agent. Note that although, for ease of discussion, the majority of the discussion in the following section is in terms of polymerase enzyme compositions, it will be appreciated that any other molecule, including other enzymes or other proteins, molecules, or nucleic acids, can be used in the methods, devices, compositions, and systems of the invention. Thus, for example, isolated nucleic acids can be loaded using the techniques described for polymerase compositions. By "polymerase compositions" as used in this section is meant to encompass compositions comprising nucleic acid templates and polymerase enzymes, as well as any associated molecules, including, for example, primers, dNTPs, and any other additives. In certain examples, the polymerase compositions comprise polymerase complexes in which a polymerase is attached to a nucleic acid template that is in some examples also further hybridized to a primer.

The methods and systems described herein improve the rate at which nucleic acid templates and any associated molecules are loaded to reaction regions on a surface as compared to typical diffusion methods in the absence of condensing agent. Typical diffusion loading methods will rely on diffusion (and gravity) to load molecules to a surface without the use of solutions with density differentials as described herein. As such, typical diffusion loading methods generally require higher concentrations of input sample to load compositions to a surface in a given amount of time. In contrast, the methods and systems described have improved efficiency of loading, such that a smaller input concentration is required to load compositions to a surface in the same given amount of time.

In general, the methods utilize a density differential between a solution bathing the surface and a solution containing the polymerase compositions to increase the efficiency of the loading of those polymerase compositions to the surface. By increasing the efficiency of loading is meant increasing the speed at which the compositions reach the surface and/or decreasing the amount of input concentration needed to occupy the surface within a given time frame.

For example, a surface is covered in a standard buffer. In certain non-limiting examples, that surface further includes a plurality of array regions. The solution containing the polymerase compositions (also referred to herein as a "spike" solution) includes a nucleic acid condensing agent and has a higher density than the standard buffer, and when the higher density spike solution is added to the standard buffer the higher density solution travels through that buffer to cover the surface as well as any array regions on that surface—as a result, the polymerase compositions in that spike solution are also carried to the surface and loaded into the array regions. The density differential allows the spike solution to carry the polymerase compositions to the surface in an efficient manner. This high density loading results in increased speed of loading of the enzyme compositions as compared to methods relying on typical diffusion controlled methods in the absence of condensing agent.

In further examples, the spike solution includes an additive that includes without limitation, polyethylene glycol (PEG) or another PEG polymer. PEG is a preferred additive since it can serve both to increase the density of the spike solution and as a nucleic acid condensing agent, as detailed above. Other large neutral or cationic polymers such as dextran and Ficoll can also be employed to both increase the density of the spike solution and as a nucleic acid condensing agent. Other exemplary additives include aminodextran, dextrin, cluster dextrin, sucrose, DMSO, glycerol, and pullulan.

In further examples, it can be desirable to load polymerase compositions that have been enriched for complexes in which a polymerase enzyme is complexed with a nucleic acid template, and that nucleic acid template is further hybridized to a primer. Thus, the spike solutions are optionally enriched for such polymerase complexes by including a step in which molecules that are not appropriate for loading are removed from the spike solution. For example, in situations in which it is desired to load polymerase complexes, the cleaning step removes "free" polymerase enzymes and primers—i.e., polymerase enzymes and primers that are not part of a polymerase-nucleic acid complex. In certain examples, this cleaning step is accomplished using particles that are able to bind to the non-complexed molecules. Such methods are of particular use in situations where high concentrations of primers and polymerases are used in order to bias complex formation. Techniques for enriching the spike solutions for polymerase complexes are described, e.g., in U.S. patent application 62/257,152.

In further examples, the nucleic acids and any associated molecules (e.g., polymerase enzymes) are loaded onto a surface, wherein the surface includes a plurality of array regions. These array regions can in still further examples include nanowells. Such nanowells may in further examples include without limitation zero mode waveguides (ZMWs). In other examples, the array regions can include nanopores.

As discussed above and in further detail herein, in some examples, compositions disclosed herein include polymerase molecules each complexed to a single template nucleic acid molecule. The single template nucleic acid molecule can comprise DNA, RNA, non-natural nucleotides, or a combination thereof. The template nucleic acid may be single stranded and/or double stranded. In some examples, the template nucleic acid is double stranded with a first end and a second end. In further examples, a first hairpin oligonucleotide connects each strand of the template nucleic acid at the first end, and a second hairpin oligonucleotide connects each strand of the template nucleic acid at the second end. In some examples, the first and second hairpin oligonucleotides are identical (also described herein as symmetrical templates), and in other examples the first and second hairpin oligonucleotides are not the same (also described herein as asymmetrical templates).

Typically, the polymerase-template complexes that are distributed onto the substrate as described herein are subsequently immobilized or bound to the substrate. For example, the polymerase can have a member of a binding pair connected to it which can bind to the other member of the binding pair attached to the substrate. In some cases the binding pair includes biotin and a protein that binds biotin such as avidin or streptavidin. Many types of binding pairs are known in the art. In some cases, an interaction between biotin and a biotin binding protein such as avidin or streptavidin is used. In some cases, an antibody-antigen interaction, for example between digoxigenin and anti-digoxigenin, is used. Reactions that form covalent linkages, for example, Spy, SNAP, or Click chemistry can be used to bind the polymerase-nucleic acid complex to the substrate. Oligonucleotide hybridization can also be used for the attachment.

Typically the polymerase enzyme is attached directly to the substrate. In other embodiments, the nucleic acid template complexed with the polymerase is attached to the substrate. Certain embodiments of template immobilization are provided, e.g., in U.S. Pat. No. 8,481,264, which is incorporated herein by reference. One skilled in the art will appreciate that there are many ways of immobilizing nucleic acids and proteins, whether covalently or non-covalently, via a linker moiety, or tethering them to an immobilized moiety. These methods are well known in the field of solid phase synthesis and micro-arrays (Beier et al., Nucleic Acids Res. 27:1970-1-977 (1999)). Non-limiting exemplary binding moieties for attaching either nucleic acids or polymerases to a solid support include streptavidin or avidin/biotin linkages, carbamate linkages, ester linkages, amide, thiolester, (N)-functionalized thiourea, functionalized maleimide, amino, disulfide, amide, and hydrazone linkages, among others. Antibodies that specifically bind to one or more reaction components can also be employed as the binding moieties. In addition, a silyl moiety can be attached to a nucleic acid and directly to a substrate such as glass using methods known in the art.

The methods and systems described herein offer several advantages over conventional methods and systems for loading molecules onto a surface. For example, for a given amount of time, the methods and systems described herein allow for smaller amounts of input molecule (such as nucleic acids or polymerase-template complexes) for the same speed of loading. In some examples, the methods and systems described herein result in about a 2× to about 100× faster loading of the polymerase composition as compared to methods and systems based on diffusion loading without the use of solutions with density differentials and condensing agents.

A further advantage of the methods and systems described herein is that a smaller input concentration of polymerase compositions is needed to achieve the same speed and level of loading as under typical diffusion loading methods without density differentials and condensing agents. A yet further advantage of methods described herein is that in general, applying a sample directly to a surface without the use of the solution differentials described herein can result in a patchy, uneven loading, due to (without being limited by mechanism) evaporation of the sample before it has a chance to evenly cover the entire surface. This is particularly true for surfaces generally used in reactions such as sequencing reactions, which generally may have surface areas of about 20-150 mm$^2$.

In some embodiments, the surface to which the polymerase compositions are loaded in accordance with any of the methods described herein has a circular geometry or a rectangular geometry. Such a surface may further comprise about 120,000 to about 2,000,000 ZMWs. In embodiments in which the surface has a circular geometry, the surface in general can comprise about 100,000, 150,000, 200,000, or 250,000 ZMWs. In embodiments in which the surface has a rectangular geometry, the surface can comprise about 750,000, 1,000,000, or 1,500,000 or more ZMWs. In further embodiments, the surface comprises about 0.5-20, 1-19, 2-18, 3-17, 4-16, 5-15, 6-14, 7-13, 8-12, or 9-11 million ZMWs. In other embodiments, such a surface may include nanopores, and any of the loading methods described herein are equally applicable to delivery of nucleic acids of any type or length to a surface comprising nanopores.

In general, the methods of loading described herein result in about a 2× to about 100× faster loading of the polymerase composition as compared to methods and systems based on diffusion loading without the use of solutions with nucleic acid condensation and density differentials. In certain embodiments, the methods of loading result in about a 5-90×, 10-80×, 15-70×, 20-60×, 25-50×, or 30-40× faster loading of the polymerase composition as compared to methods and systems based on diffusion loading without the use of solutions with nucleic acid condensation and density or other solution differentials.

As noted, the methods leverage a density differential between a spike solution and the solution covering a surface to increase the efficiency with which compositions are loaded to the surface. In specific embodiments, a surface is covered in a standard buffer. In certain non-limiting examples, that surface further includes a plurality of array regions, which may in turn comprise nanowells (nanoscale wells). Those nanowells may comprise without limitation ZMWs. The spike solution containing the polymerase compositions has a higher density than the standard buffer, such that when the higher density spike solution is added to buffer the higher density solution travels through that buffer to cover the surface as well as any array regions on that surface. As a result, the polymerase compositions in that spike solution are also carried to the surface and loaded into any array regions on that surface. The density differential allows the spike solution to carry the polymerase compositions to the surface in an efficient manner. This high density loading results in increased speed of loading of the polymerase compositions as compared to methods relying on typical diffusion controlled methods in the absence of nucleic acid condensing/density increasing components.

The density of the spike solution can be heightened in comparison to the standard buffer covering the surface using additives known in the art and described herein. In preferred embodiments, PEG serves both to increase the density of the spike solution and to condense nucleic acids. PEG can be included in the spike solution at concentrations of between about 1-20% by volume (v/v), e.g., at concentrations of about 2-18%, 5-15%, 8-10%, or 3-10% by volume. In some embodiments, a combination of PEG and at least one cation is employed to condense the nucleic acids. Suitable PEGs (and other PEG polymers) and exemplary cations have been detailed above, as have suitable concentration ranges. In other embodiments, a density enhancing additive can be provided in addition to a nucleic acid condensing agent (e.g., a combination of PEG, polycation, or another condensing agent and a density modifying additive can be employed). Exemplary density modifying additives include a neutral and hydrophilic polysaccharide, a highly branched, high-mass polysaccharide, dextran, aminodextran, dextrin, cluster dextrin, Ficoll, sucrose, PEG, DMSO, glycerol, and pullulan. In some embodiments, the spike solution comprises a volume excluding buffer. As will be appreciated, additives can be included in the solution at any concentration useful for increasing the density of the solution. Such additives may be included at concentrations of between about 1-20% by volume (v/v). In further embodiments, such additives are included at concentrations of about 2-18%, 5-15%, 8-10%, or 3-10% by volume.

As discussed herein, the loading of the polymerase compositions using the spike solution (also referred to herein as "distributing" the polymerase compositions) occurs about 2-50 fold faster as compared to distributing by diffusion without the spike solution. In further embodiments, the distributing with the spike solution occurs at about a 5-45, 10-40, 15-35, 20-30 fold faster rate as compared to distributing without the spike solution. In still further embodiments, the distributing with the spike solution occurs at least 2, 5, 10, 20, 50, 75, 100, 150, or 200-fold faster as compared to distributing by diffusion without the spike solution.

In further embodiments, the spike solution has a lower volume than that of the buffer bathing the surface onto which the polymerase compositions are to be distributed. In some embodiments, the spike solution has a volume that is about 1% to about 20% of the volume of the buffer. In further embodiments, the spike solution has a volume of about 1-30%, 5-15%, 10-25%, or 15-20% of the volume of the buffer. In yet further embodiments, the spike solution has a volume of about 2%, 5%, 10%, 15%, 20%, 25%, 30%, 35%, 40%, 45%, or 50% of the volume of the buffer. In still further embodiments, the volume of the spike solution is in a ratio to the volume of the buffer of about 1:5, 1:7, 1:9, 1:10, 1:12, 1:15, 1:20, 1:30, 1:40, or 1:50.

In further embodiments, increasing salt concentrations can further enhance density loading as described herein. In certain embodiments, the salt includes without limitation potassium acetate, sodium acetate, sodium chloride, potassium chloride, or any other salt generally used in buffer solutions. In still further embodiments, the high density loading methods utilize spike solutions comprising about 100-600, 150-550, 200-500, 250-450, or 300-400 mM salt.

In some embodiments, and in accordance with any of the above, high density loading methods as described herein include providing a surface comprising an array of nanowells. These nanowells may include in further embodiments ZMWs. The surface with the nanowells further comprises a standard buffer solution, including any standard buffers used for example in sequencing reactions and that are known in the art. In certain embodiments, the standard buffer includes a potassium salt and has a pH in the range of 7-9. In some embodiments, the buffer may include Tris acetate or Tris-HCl as exemplary embodiments. A spike solution with a higher density than that of the standard buffer and containing nucleic acids (e.g., complexes of polymerase enzymes attached to nucleic acid templates that are further hybridized with primers) is applied to the standard buffer. The higher density of the spike solution causes it to travel through the standard buffer to the nanowells and load the nucleic acids or polymerase complexes into the nanowells at a faster rate compared to that seen when there is no density differential between the loading solution and the standard buffer.

The density of the spike solution can be of any density that is higher than that of the standard buffer. In some non-limiting embodiments, the density of the spike solution is 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.4, 3.6, 3.8, 4.0, 4.2, 4.4, 4.6, 4.8, 5.0× higher than the density of the standard buffer. In further embodiments, the spike solution is about 0.5-3×, 0.6-2.5×, 0.8-2.0×, 1.0-1.5× higher than the density of the standard buffer. In still further embodiments, the density (also referred to as specific gravity) of the spike solution is about 2-20% higher than that of the standard buffer. In yet further embodiments, the density of the spike solution is about 1.5-30, 2-28, 3-26, 4-24, 5-22, 6-20, 7-18, 8-16, 9-14, 10-12% higher than the density of the standard buffer. In still further embodiments, the density of the spike solution is about 1-5, 1.1-1.5, 1.2-2.0, 1.3-2.5, 1.4-3.0, 1.5-3.5, 1.6-4.0, 1.7-4.5, 1.8-5, 1.9-5.5, 2.0-6.0 g/cm$^3$.

In some embodiments, the distributing of the molecules to the surface in any of the methods described herein and in accordance with any of the above is complete in about 0.5 to about 5 hours. In still further embodiments, the distributing is complete in about 1-4.5, 1.5-4, 1-3, or 2-3.5 hours.

In yet further embodiments, the amount of input sample, including any one or combination of input nucleic acid templates, polymerase molecules, and primers, produces the same amount of loading in less time than is seen without the use of a high density spike solution. In other words, for the same given amount of time, less input sample is needed to load the same number of molecules to the surface when using the high density solution methods described herein than when using diffusion controlled methods that do not utilize solutions of differing density.

In still further embodiments, among the molecules that are loaded to the surface using the methods described herein are nucleic acid templates, generally as part of complexes with polymerase molecules. Such nucleic acid templates can include any nucleic acid molecules known in the art and described herein. In some embodiments, the templates have lengths of about 50 to 600 nucleotides. In another embodiment, the nucleic acids are 300 to 600 or 200 to 20000 nucleotides in length. In yet another embodiment, the nucleic acid templates are 10-100, 50-100, 50-300, 100-200, 200-300, 50-400, 100-400, 200-400, 400-500, 400-600, 500-600, 50-1000, 100-1000, 200-1000, 300-1000, 400-1000, 500-1000, 600-1000, 700-1000, 700-900, 700-800, 800-1000, 900-1000, 1500-2000, 1750-2000, 50-2000, 100-25000, 200-24000, 300-23000, 400-22000, 500-21000, 600-20000, 700-19000, 800-18000, 900-17000, 1000-16000, 1100-15000, 1200-14000, 1300-13000, 1400-12000, 1500-11000, 1600-10000, 1700-9000, 1800-8000, 1900-7000, 2000-6000, 2100-5000, 2200-4000, 2300-3000, 10000-30000, 12000-28000, 14000-26000, 16000-24000, 18000-22000, or 19000-20000 nucleotides in length. Optionally, the nucleic acid templates are at least 5 kb in length, e.g., at least 10 kb, at least 15 kb, at least 20 kb, at least 25 kb, at least 30 kb, at least 40 kb, at least 50 kb, at least 70 kb, at least 100 kb, at least 200 kb, at least 500 kb, or even at least 1000 kb in length. In further embodiments, the nucleic acid templates are part of polymerase-template complexes. In yet further embodiments, the nucleic acid templates are themselves further hybridized to primers.

In further embodiments and in accordance with any of the above, the spike solution has a greater viscosity than the buffer into which it is placed. "Viscosity" as used herein refers to dynamic viscosity, the resistance of a fluid to shearing flow. The unit of viscosity in SI is the Poiseuille (PI) [1 PI=1 Pa*s] or the Poise (P) [1P=0.100 kg/ms]. In general, the viscosity of the spike solution is no more than 10× that of the viscosity of water. In certain embodiments, the viscosity of the spike solution is no more than 8×, 6×, 4×, or 2× that of water. (Water has a viscosity of approximately 1 centipoise (cP).) In further embodiments, the balance between the viscosity and density of the spike solution is such that the efficiency of the loading of spike solution (and the molecules that it contains) is increased over that of solutions that do not have that balance between viscosity and density. In further embodiments, the viscosity of the spike solution is about 1.5-10, 2-9, 2.5-8, 3-7, 3.5-6, 4-5 cP. In still further embodiments, the density of the spike solution is from about 1-5, 1.1-1.5, 1.2-2.0, 1.3-2.5, 1.4-3.0, 1.5-3.5, 1.6-4.0, 1.7-4.5, 1.8-5, 1.9-5.5, 2.0-6.0 g/cm$^3$ and a viscosity of about 2-12, 3-11, 4-10, 5-9, 6-8 cP.

Loading One Nucleic Acid Per Array Region

One difficulty in performing single molecule analyses occurs in loading the reaction/observation region of single molecule analysis devices with the molecules of interest (e.g., template or other analyte and/or enzyme). Loading two or more molecules of interest into a ZMW or other small observation volume tends to complicate any analysis of signals observed from the double (or more than double)-loaded region. This is because two (or more) sets of signals may simultaneously be observed from the ZMW or other observation volume, meaning that the signals from the ZMW would have to be deconvoluted before data from the observation region could be used. Data from double (+) loaded ZMWs can be recognized by various data analysis methods. Data from mis-loaded ZMWs or other relevant observation volumes can be discarded, e.g., where it cannot be deconvoluted; typically a deconvolution algorithm is able to reclaim useful data from a portion of the total data produced by double(+) loaded ZMWs.

To reduce the incidence of multiple molecule loading events in the relevant reaction/observation volume(s) of the array, it is typical in the art to substantially "under-load" the array with the analyte molecules of interest. Random distribution of molecules into the array results in one or fewer molecules being loaded into most reaction/observation volumes when fewer than 20% of all observation volumes are loaded. The highest possible percentage of single-molecule occupancies is 36.8% when about 64% of all observation volumes are loaded. This type of loading is referred to as "Poisson-limited" analyte loading, meaning that few enough molecules are added to the array so that a Poisson-style random statistical distribution of the analytes into the array results in one or fewer analytes per observation volume in most cases. In the ZMW context, state of the art yields for single-molecule occupancies of approximately 36% have been obtained for a range of ZMW diameters (e.g., 70-100 nm). See, Foquet et al. (2008) "Improved fabrication of zero-mode waveguides for single-molecule detection" *Journal of Applied Physics* 103, 034301. For this degree of loading, about 37% of the ZMWs in a typical ZMW array are not loaded (e.g., have no analyte molecules).

Higher loading densities would permit the simultaneous analysis of more analyte molecules in the array, increasing the throughput of such systems while simultaneously decreasing analysis costs. Various techniques for achieving high loading densities are described, e.g., in U.S. Pat. No. 8,906,831 and U.S. patent application Ser. No. 15/078,915 filed Mar. 23, 2016, each of which is hereby incorporated by reference in its entirety. Such techniques can be facilitated by inclusion of a nucleic acid condensing agent as described herein.

Further, without limitation to any particular mechanism, condensation of a large nucleic acid (e.g., greater than 8 kb, greater than 10 kb, greater than 15 kb, greater than 20 kb, greater than 30 kb, greater than 40 kb, greater than 50 kb, greater than 70 kb, greater than 100 kb, greater than 200 kb, greater than 500 kb, or even greater than 1000 kb) can result in a condensed molecule that excludes enough volume to disfavor immobilization of a second nucleic acid in the same reaction region or nanoscale well. Thus, in some embodiments, after distribution of the nucleic acids (e.g., polymerase-template complexes), at least 38% of the nanoscale wells (or other array regions) are occupied by a single immobilized nucleic acid (e.g., a single immobilized polymerase-template complex), e.g., at least 50% or at least 75% of the wells or regions. Loading can be bead-assisted, by diffusion, or by density spike as detailed above. The degree of condensation can be modulated by adjusting solution conditions, e.g., type of PEG, concentration of PEG, and/or concentration of monovalent and divalent ions, and thereby affect the extent of volume excluded by a nucleic acid. The nanoscale wells (e.g., ZMWs) optionally have a critical dimension of 50 nm-400 nm or 50 nm-300 nm, e.g., the diameter of the top opening of the well or the diameter of the base of the well.

Additional size exclusion effects can be achieved, for example, by attaching one or more particles to the nucleic acid (including, e.g., to another molecule bound in turn to the nucleic acid, such as a polymerase molecule). Attachment is optionally covalent (e.g., through a coupling molecule engineered with a cleavable linkage to allow dissociation of the particle from the template after immobilization) or noncovalent (e.g., through hybridization, e.g., polyA on template to poly-dT coated beads, or through non-specific ionic interaction). Suitable particles for attachment to nucleic acids include, but are not limited to, magnetic or non-magnetic beads or particles of any size, biological molecules such as proteins, DNA or oligomers, complexes, and aggregates thereof. Typically, the overall size of a suitable particle is slightly smaller or slightly larger than the bottom ZMW diameter or top diameter (or than the critical dimension of another array region). A few specific examples of suitable particles are magnetic or non-magnetic dT beads (e.g., 50 to 300 nm), polymer particles functionalized with dT or another oligo or with carboxyl groups (e.g., Ampure® beads), histones or other basic proteins with affinity for DNA, engineered self-assembling polyhedral protein shell with DNA binding groups, and viral (hollow) capsids functionalized with DNA binding groups. Particles can be employed solely for their size exclusion benefits, or the particles (e.g., beads) can be employed to assist in loading as detailed above (e.g., under the influence of a gravitational or magnetic field) in addition to providing size exclusion benefits.

Where coupling agent is provided for immobilization of the nucleic acids, e.g., at the base of nanoscale wells, controlling the density or number of the coupling agent on the surface can assist in attaining the desired occupancy. For example, density or number of the coupling agent on the surface can be adjusted such that enough agent is available to readily bind to the first nucleic acid to encounter the base of a nanoscale well, but such that occupancy of the well by that first nucleic acid is sufficient to occlude accessibility of coupling agent in that well by other nucleic acids. In one embodiment, there is one coupling agent at the base of a nanoscale well. In some embodiments, the density or number of the coupling agent will be some fraction of the maximum possible density or number of the coupling agent on the surface in a nanoscale well.

Templates and Other Nucleic Acids

The practice of the inventions described in the present disclosure may employ, unless otherwise indicated, conventional techniques and descriptions of organic chemistry, polymer technology, molecular biology (including recombinant techniques), cell biology, biochemistry, and immunology, which are within the skill of the art. Such conventional techniques include nucleic acid synthesis, isolation and/or manipulation, polymer array synthesis, hybridization, ligation, phage display, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Sambrook et al., Molecular Cloning—A Laboratory Manual (3rd Ed.), Vol. 1-3, Cold Spring Harbor Laboratory, Cold Spring Harbor, N.Y., 2000, Current Protocols in Molecular Biology, F. M. Ausubel et al., eds., Current Protocols, a joint venture between Greene Publishing Associates, Inc. and John Wiley & Sons, Inc., (supplemented through 2016), Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, N.Y., Gait, "Oligonucleotide Synthesis: A Practical Approach" 1984, IRL Press, London, Nelson and Cox (2000), Lehninger, Principles of Biochemistry 3rd Ed., W. H. Freeman Pub., New York, N.Y. and Berg et al. (2002) Biochemistry, 5th Ed., W. H. Freeman Pub., New York, N.Y., all of which are herein incorporated in their entirety by reference for all purposes.

The nucleic acids employed in the practice of the invention can be fully or partially double-stranded or can be single-stranded. Suitable nucleic acids include, but are not limited to, SMRTbells™ (circular nucleic acids having a double-stranded central region and single-stranded hairpin ends), double-stranded circular DNA molecules (e.g., nicked or gapped double-stranded circular DNA molecules, e.g., nicked or gapped plasmids), and linear molecules (e.g., genomic DNA fragments).

Nucleic acids, including template nucleic acids, can be prepared using techniques well known in the art, from essentially any desired sample. For further discussion of circular templates, including, e.g., simple circles and SMRTbells™ (circular nucleic acids having a double-stranded central region and single-stranded hairpin ends), see, e.g., U.S. Pat. No. 8,236,499 "Methods and Compositions for Nucleic Acid Sample Preparation," U.S. Pat. No. 8,153,375 "Compositions and Methods for Nucleic Acid Sequencing," and Travers et al. (2010) Nucl. Acids Res. 38(15):e159, each of which is incorporated herein by reference in its entirety for all purposes). As noted, the methods can be particularly useful for loading of large template molecules. Thus, in some embodiments, the nucleic acid templates are at least 5000, 10000, 15000, 20000, 25000, 30000, 40000, 50000, 60000, 70000, 80000, 90000, 100,000, 120,000, 130,000, 140,000, 150,000, 200,000, 500,000, or 1,000,000 nucleotides in length.

Any of the methods and complexes described herein can include template nucleic acid molecules, often as part of the polymerase enzyme complexes described herein. In general, a template nucleic acid is a molecule for which the complementary sequence is (or can be) synthesized in a polymerase reaction. As will be appreciated, template sequences can be of any length or structure. In some cases, the template nucleic acid is linear; in some cases, the template nucleic acid is circular. The template nucleic acid can be DNA, RNA, and/or a non-natural RNA or DNA analog. Any template nucleic acid that is suitable for replication by a polymerase enzyme can be used in the methods and systems described herein.

In some embodiments, the template nucleic acids used in methods and compositions of the present invention comprise nucleic acids obtained from a sample. The sample may comprise any number of things, including, but not limited to, bodily fluids (including, but not limited to, blood, urine, serum, lymph, saliva, anal and vaginal secretions, perspiration and semen) and cells of virtually any organism, with mammalian samples being preferred and human samples being particularly preferred; environmental samples (including, but not limited to, air, agricultural, water and soil samples); biological warfare agent samples; research samples (e.g., in the case of nucleic acids, the sample may be the products of an amplification reaction, including both target and signal amplification, such as PCR amplification reactions; purified samples, such as purified genomic DNA, RNA preparations, raw samples (bacteria, virus, genomic DNA, etc.); as will be appreciated by those in the art, virtually any experimental manipulation may have been done on the samples.

In further embodiments, nucleic acid molecules are obtained from a sample and fragmented for use in (or prior to use in) methods of the invention as template nucleic acids.

The fragments may be single or double stranded and may further be modified in accordance with any methods known in the art and described herein. Template nucleic acids may be generated by fragmenting source nucleic acids, such as genomic DNA, using any method known in the art. In one embodiment, shear forces during lysis and extraction of genomic DNA generate fragments in a desired range. Also encompassed by the present disclosure are methods of fragmentation utilizing restriction endonucleases.

As will be appreciated, the template nucleic acids may be generated from a source nucleic acid, such as genomic DNA, by fragmentation to produce fragments of a specific size. The target nucleic acids can be, for example, from about 10 to about 50,000 nucleotides in length, or from about 10 to about 20,000 nucleotides in length. In one embodiment, the fragments are 50 to 600 nucleotides in length. In another embodiment, the fragments are 300 to 600 or 200 to 2000 nucleotides in length. In yet another embodiment, the fragments are 10-100, 50-100, 50-300, 100-200, 200-300, 50-400, 100-400, 200-400, 400-500, 400-600, 500-600, 50-1000, 100-1000, 200-1000, 300-1000, 400-1000, 500-1000, 600-1000, 700-1000, 700-900, 700-800, 800-1000, 900-1000, 1500-2000, 1750-2000, and 50-2000 nucleotides in length. In further embodiments, the fragments are at least 5000, 10000, 15000, 20000, 25000, 30000, 40000, 50000, 60000, 70000, 80000, 90000, 100,000, 120,000, 130,000, 140,000, or 150,000 nucleotides in length. In yet further embodiments, the nucleic acid templates are 10-100, 50-100, 50-300, 100-200, 200-300, 50-400, 100-400, 200-400, 400-500, 400-600, 500-600, 50-1000, 100-1000, 200-1000, 300-1000, 400-1000, 500-1000, 600-1000, 700-1000, 700-900, 700-800, 800-1000, 900-1000, 1500-2000, 1750-2000, 50-2000, 100-25000, 200-24000, 300-23000, 400-22000, 500-21000, 600-20000, 700-19000, 800-18000, 900-17000, 1000-16000, 1100-15000, 1200-14000, 1300-13000, 1400-12000, 1500-11000, 1600-10000, 1700-9000, 1800-8000, 1900-7000, 2000-6000, 2100-5000, 2200-4000, 2300-3000, 5000-20000, 10000-30000, 12000-28000, 14000-26000, 16000-24000, 18000-22000, 19000-20000 nucleotides in length. In yet further embodiments, the nucleic acid templates are at least 5000, 10000, 15000, 20000, 25000, 30000, 40000, 50000, 60000, 70000, 80000, 90000, 100,000, 120,000, 130,000, 140,000, 150,000, 200,000, 500,000, or 1,000,000 nucleotides in length. In further embodiments, the nucleic acids are part of polymerase-template complexes. In yet further embodiments, the nucleic acid templates are themselves further hybridized to primers.

In some cases, the template sequence may be a linear single or double stranded nucleic acid sequence. In still other embodiments, the template may be provided as a circular or functionally circular construct that allows redundant processing of the same nucleic acid sequence by the synthesis complex. Use of such circular constructs has been described in, e.g., U.S. Pat. No. 7,315,019 and U.S. patent application Ser. No. 12/220,674, filed Jul. 25, 2008, and alternate functional circular constructs are also described in US Pat. App. Pub. No. 20090298075, the full disclosures of each of which are incorporated herein by reference in their entirety for all purposes and in particular for all teachings related to template nucleic acid constructs. Briefly, such alternate constructs include template sequences that possess a central double stranded portion that is linked at each end by an appropriate linking oligonucleotide, such as a hairpin loop segment (SMRTbells™). Such structures not only provide the ability to repeatedly replicate a single molecule (and thus sequence that molecule), but also provide for additional redundancy by replicating both the sense and antisense portions of the double stranded portion. In the context of sequencing applications, such redundant sequencing provides great advantages in terms of sequence accuracy.

In further aspects, the template nucleic acid used in the compositions of the present invention includes: a double stranded nucleic acid segment having a first and second end; a first hairpin oligonucleotide connecting each strand of the single template nucleic acid at the first end; and a second hairpin oligonucleotide connecting each strand of the single template nucleic acid at the second end. In some embodiments, the first hairpin and second hairpin oligonucleotide are identical. In other embodiments, the first hairpin and second hairpin oligonucleotides are not identical—in other words, the template nucleic acid, despite being an alternate circular construct, is nevertheless asymmetrical. In further embodiments, the first hairpin oligonucleotide includes a primer binding site whereas the second hairpin oligonucleotide includes a capture adapter (or vice versa). The capture adapter is generally of a sequence that can be used to enrich a population for the hairpins of choice—for example, in some embodiments, the capture adapter comprises a polyA sequence, thereby allowing capture using beads or column chromatography utilizing polyT sequences. In some embodiments, the capture adapter comprises at least one methoxy residue. In further embodiments, the capture adapter is complementary to an oligonucleotide attached to a bead, which can in further embodiments be a magnetic bead that can be used to enrich a population for template nucleic acids containing the capture adapter. In some embodiments in which the population of templates includes templates with different adapters or in which each template comprises a different adapter at each end, different beads can be used which contain oligonucleotides complementary to the different adapters. Thus, for templates with two different adapters, two different beads can be used. For populations containing a plurality of different adapters, a concomitant number of different types of beads can be used that are directed to those adapters. In other embodiments, the same bead can contain different oligonucleotides complementary to the different adapters in the population of templates, such that the same bead can capture different adapters (and their associated templates).

In still further embodiments, the first or second hairpin comprises a self-primed adapter sequence in which the primer is part of the adapter. In such embodiments, an additional oligonucleotide primer is not needed to allow a polymerase molecule to begin replicating the template.

In other embodiments, the nucleic acid template contains only a single hairpin at one end or the other.

The polymerase enzymes of use in the methods and compositions described herein generally require a primer. While in most cases an oligonucleotide primer is used, in some cases a protein such as a terminal protein can acts as a primer. Oligonucleotide primers are generally complementary to a portion of the template nucleic acid. The primers can comprise naturally occurring RNA or DNA oligonucleotides. The primers may also be synthetic analogs. The primers may have alternative backbones as described above. The primers may also have other modifications, such as the inclusion of heteroatoms, the attachment of labels, such as dyes, or substitution with functional groups which will still allow for base pairing and for recognition by the enzyme. Primers can select tighter binding primer sequences, e.g., GC rich sequences, as well as employ primers that include within their structure non-natural nucleotides or nucleotide analogs, e.g., peptide nucleic acids (PNAs) or locked nucleic acids (LNAs), that can demonstrate higher affinity pairing with the template. The primers can also be selected to influence the kinetics of the polymerase reaction through the use of length, nucleotide content, and/or any of the modifications discussed above.

In other embodiments, self-priming templates are employed. For example, a SMRTbell™ including a self-primed adapter sequence can be employed, as noted above. As another example, a double-stranded template including at least one nick or gap can be employed (e.g., a nicked or gapped double-stranded plasmid).

Polymerases

Many of the methods and compositions of the present disclosure utilize polymerase enzymes (also referred to herein as "polymerases"). Any suitable polymerase enzyme can be used in the systems and methods disclosed herein. Suitable polymerases include DNA dependent DNA polymerases, DNA dependent RNA polymerases, RNA dependent DNA polymerases (reverse transcriptases), and RNA dependent RNA polymerases. In certain embodiments, the polymerases used in the methods and compositions of the present invention are strand-displacing polymerases.

As disclosed in further detail herein, polymerases of use in the presently disclosed methods may include modifications that improve certain characteristics of the enzyme, including processivity, resistance to photodamage, and conduciveness to immobilization. In certain aspects, polymerases used in the methods and systems disclosed herein include a linker, motif (e.g., a biotin ligase recognition sequence), or domain through which the polymerases (and any other molecules they are complexed with, such as template nucleic acids) can be immobilized onto a surface.

DNA polymerases are sometimes classified into six main groups based upon various phylogenetic relationships, e.g., with E. coli Pol I (class A), E. coli Pol II (class B), E. coli Pol III (class C), Euryarchaeotic Pol II (class D), human Pol beta (class X), and E. coli UmuC/DinB and eukaryotic RAD30/xeroderma pigmentosum variant (class Y). For a review of recent nomenclature, see, e.g., Burgers et al. (2001) "Eukaryotic DNA polymerases: proposal for a revised nomenclature" J Biol Chem. 276(47):43487-90. For a review of polymerases, see, e.g., Hübscher et al. (2002) "Eukaryotic DNA Polymerases" Annual Review of Biochemistry Vol. 71: 133-163; Alba (2001) "Protein Family Review: Replicative DNA Polymerases" Genome Biology 2(1):reviews 3002.1-3002.4; and Steitz (1999) "DNA polymerases: structural diversity and common mechanisms" J Biol Chem 274:17395-17398. The basic mechanisms of action for many polymerases have been determined. The sequences of literally hundreds of polymerases are publicly available, and the crystal structures for many of these have been determined, or can be inferred based upon similarity to solved crystal structures of homologous polymerases. For example, the crystal structure of Φ29, a preferred type of parental enzyme to be modified according to the invention, is available.

In addition to wild-type polymerases, chimeric polymerases made from a mosaic of different sources can be used. For example, Φ29 polymerases made by taking sequences from more than one parental polymerase into account can be used as a starting point for mutation to produce the polymerases used in methods described herein. Chimeras can be produced, e.g., using consideration of similarity regions between the polymerases to define consensus sequences that are used in the chimera, or using gene shuffling technologies in which multiple Φ29-related polymerases are randomly or semi-randomly shuffled via available gene shuffling techniques (e.g., via "family gene shuffling"; see Crameri et al. (1998) "DNA shuffling of a family of genes from diverse species accelerates directed evolution" Nature 391:288-291; Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296). In these methods, the recombination points can be predetermined such that the gene fragments assemble in the correct order. However, the combinations, e.g., chimeras, can be formed at random. For example, using methods described in Clarkson et al., five gene chimeras, e.g., comprising segments of a Phi29 polymerase, a PZA polymerase, an M2 polymerase, a B103 polymerase, and a GA-1 polymerase, can be generated. Appropriate mutations to improve branching fraction, increase closed complex stability, or alter reaction rate constants can be introduced into the chimeras.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. As noted, polymerases have also been modified to confer improvements in specificity, processivity, and improved retention time of labeled nucleotides in polymerase-DNA-nucleotide complexes (e.g., WO 2007/076057 Polymerases For Nucleotide Analogue Incorporation by Hanzel et al. and WO 2008/051530 Polymerase Enzymes And Reagents For Enhanced Nucleic Acid Sequencing by Rank et al.), to alter branch fraction and translocation (e.g., US Pub. No. 20100075332 entitled "Engineering Polymerases And Reaction Conditions For Modified Incorporation Properties"), to increase photostability (e.g., US Pub. No. 20100093555 entitled "Enzymes Resistant to Photodamage"), and to improve surface-immobilized enzyme activities (e.g., WO 2007/075987 Active Surface Coupled Polymerases by Hanzel et al. and WO 2007/076057 Protein Engineering Strategies To Optimize Activity Of Surface Attached Proteins by Hanzel et al.). In some cases, the polymerase is modified in order to more effectively incorporate desired nucleotide analogs, e.g. analogs having four or more phosphates in their polyphosphate chain. Enzymes mutated to more readily accept nucleotide analogs having such properties are described, for example in the applications described above and in US 20120034602—Recombinant Polymerases for Improved Single Molecule Sequencing; US 20100093555—Enzymes Resistant to Photodamage; US 20110189659—Generation of Modified Polymerases for Improved Accuracy in Single Molecule Sequencing; US 20100112645—Generation of Modified Polymerases for Improved Accuracy in Single Molecule Sequencing; US 2008/0108082—Polymerase enzymes and reagents for enhanced nucleic acid sequencing; and US 20110059505—Polymerases for Nucleotide Analogue Incorporation which are incorporated herein by reference in their entirety for all purposes.

Many polymerases that are suitable for modification are available, e.g., for use in sequencing, labeling and amplification technologies. For example, human DNA Polymerase Beta is available from R&D systems. DNA polymerase I is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. Φ29 DNA polymerase is available from e.g., Epicentre. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include Phusion™ High-Fidelity DNA Polymerase, available from New England Biolabs; GoTaq® Flexi DNA Polymerase, available from Promega; RepliPHI™ Φ29 DNA Polymerase, available from Epicentre Biotechnologies; PfuUltra™ Hotstart DNA Polymerase, available from Stratagene; KOD HiFi DNA Polymerase, available from Novagen; and many others. Biocompare(dot) com provides comparisons of many different commercially available polymerases.

DNA polymerases that are preferred substrates for mutation to improve desired properties (e.g., for use in single molecule sequencing, include, e.g., Taq polymerases, exonuclease deficient Taq polymerases, E. coli DNA Polymerase 1, Klenow fragment, reverse transcriptases, Φ29-related polymerases including wild type Φ29 polymerase and derivatives of such polymerases such as exonuclease deficient forms, T7 DNA polymerase, T5 DNA polymerase, an RB69 polymerase, etc.

In one aspect, the polymerase of use in the methods and compositions described herein is a modified Φ29-type DNA polymerase. For example, the modified recombinant DNA polymerase can be homologous to a wild-type or exonuclease deficient Φ29 DNA polymerase, e.g., as described in U.S. Pat. Nos. 5,001,050, 5,198,543, or 5,576,204. Alternately, the modified recombinant DNA polymerase can be homologous to other Φ29-type DNA polymerases, such as B103, GA-1, PZA, Φ15, BS32, M2Y, Nf, G1, Cp-1, PRD1, PZE, SF5, Cp-5, Cp-7, PR4, PR5, PR722, L17, Φ21, or the like. For nomenclature, see also, Meijer et al. (2001) "Φ29 Family of Phages" Microbiology and Molecular Biology Reviews, 65(2):261-287. Suitable polymerases are described, for example, in U.S. Patent application publications 2007-0196846, 2008-0108082, 2010-0075332, 2010-0093555, 2010-0112645, 2011-0189659, 2012-0034602, 2013-0217007, 2014-0094374, and 2014-0094375, each of which is incorporated herein by reference in its entirety for all purposes.

In further embodiments, the polymerase enzyme used in the methods described herein includes RNA dependent DNA polymerases or reverse transcriptases. Suitable reverse transcriptase enzymes include HIV-1, M-MLV, AMV, and Telomere Reverse Transcriptase. Reverse transcriptases also allow for the direct sequencing of RNA substrates such as messenger RNA, transfer RNA, non-coding RNA, ribosomal RNA, micro RNA or catalytic RNA.

Many native DNA polymerases have a proof-reading exonuclease function which can yield substantial data analysis problems in processes that utilize real time observation of incorporation events as a method of identifying sequence information, e.g., single molecule sequencing applications. Even where exonuclease activity does not introduce such problems in single molecule sequencing, reduction of exonuclease activity can be desirable since it can increase accuracy (in some cases at the expense of readlength).

Accordingly, polymerases for use in the above techniques optionally include one or more mutations (e.g., substitutions, insertions, and/or deletions) relative to the parental polymerase that reduce or eliminate endogenous exonuclease activity. For example, relative to wild-type Φ29 DNA polymerase, one or more of positions N62, D12, E14, T15, H61, D66, D169, K143, Y148, and H149 is optionally mutated to reduce exonuclease activity in a recombinant Φ029 polymerase. Exemplary mutations that can reduce exonuclease activity in a recombinant Φ29 polymerase include, e.g., N62D, N62H, D12A, T15I, E14I, E14A, D66A, K143D, D145A and D169A substitutions, as well as addition of an exogenous feature at the C-terminus (e.g., a polyhistidine tag). See, e.g., US patent application publication 2014/0094375, incorporated herein by reference in its entirety for all purposes, for the sequence of wild-type Φ29 polymerase.

Applications: Sequencing

The methods, devices, and compositions of the invention are particularly useful for single molecule sequencing methods, and specifically single molecule sequencing by incorporation in real time, because the methods and compositions of the present disclosure provide a way to efficiently establish a high density array of reaction regions occupied by nucleic acids (including, e.g., by polymerase compositions). As discussed above, the loading of the nucleic acids into the array is accomplished more quickly and with lower concentrations of input sample than is generally required in typical loading methods that rely on diffusion in the absence of a condensing agent. These methods thus reduce the time and resources required to establish the array for use in methods such as sequencing methods. In specific embodiments, the methods result in loading an array of reaction regions such that a single nucleic acid (or a single polymerase enzyme complexed with a nucleic acid template and optionally a primer) occupy a plurality of the reaction regions, thus allowing for single molecule sequencing from those reaction regions. In addition, as detailed above, certain embodiments of the present invention provide a way to achieve high density single molecule loading, which allows single molecule analysis to be conducted more efficiently and with greater speed because there will be fewer "unusable" regions on a substrate surface for the sequencing reaction (i.e., regions that have no or multiple polymerase compositions loaded, which provide either no information (for the empty regions) or sequencing information that must be deconvoluted to account for the multiply loaded molecules).

Sequence analysis can be performed after distribution of the nucleic acids to (and their optional immobilization in) the array regions. As noted in the examples herein, condensing agent is typically removed (e.g., by washing with a suitable buffer) prior to determination of the sequence of the nucleic acids.

In some aspects, the present invention includes methods of analyzing the sequence of template nucleic acids. In such aspects, the sequence analysis typically employs template dependent synthesis in identifying the nucleotide sequence of the template nucleic acid. Nucleic acid sequence analysis that employs template dependent synthesis identifies individual bases, or groups of bases, as they are added during a template mediated synthesis reaction, such as a primer extension reaction, where the identity of the base is required to be complementary to the template sequence to which the primer sequence is hybridized during synthesis. Other such processes include ligation driven processes, where oligo- or polynucleotides are complexed with an underlying template sequence, in order to identify the sequence of nucleotides in that sequence. Typically, such processes are enzymatically mediated using nucleic acid polymerases, such as DNA polymerases, RNA polymerases, reverse transcriptases, and the like, or other enzymes such as in the case of ligation driven processes, e.g., ligases.

Sequence analysis using template dependent synthesis can include a number of different processes. For example, in embodiments utilizing sequence by synthesis processes, individual nucleotides or nucleotide analogs are identified iteratively as they are added to the growing primer extension product.

For sequencing processes that rely upon monitoring of the incorporation of nucleotides into growing nascent strands being synthesized by the complex, the progress of the reaction through these steps can of significant importance. In particular, for certain "real-time" nucleotide incorporation monitoring processes, the detectability of the incorporation event is improved based upon the amount of time the nucleotide is incorporated into and retained within the synthesis complex during its ultimate incorporation into a primer extension product. By way of example, in certain exemplary processes, the presence of the nucleotide in the synthesis complex is detected either by virtue of a focused observation of the synthesis complex, or through the use of interactive labeling techniques that produce characteristic signals when the nucleotide is within the synthesis complex. See, e.g., Levene, et al., Science 299:682-686, January 2003, and Eid, J. et al., Science, 323(5910), 133-138 (2009), the full disclosures of which are incorporated herein by reference in their entirety for all purposes.

In further aspects, the methods of the present invention include steps from any single molecule sequencing methods known in the art. See, e.g., Rigler, et al., DNA-Sequencing at the Single Molecule Level, Journal of Biotechnology, 86(3): 161 (2001); Goodwin, P. M., et al., Application of Single Molecule Detection to DNA Sequencing. Nucleosides & Nucleotides, 16(5-6): 543-550 (1997); Howorka, S., et al., Sequence-Specific Detection of Individual DNA Strands using Engineered Nanopores, Nature Biotechnology, 19(7): 636-639 (2001); Meller, A., et al., Rapid Nanopore Discrimination Between Single Polynucleotide Molecules, Proceedings of the National Academy of Sciences of the United States of America, 97(3): 1079-1084 (2000); Driscoll, R. J., et al., Atomic-Scale Imaging of DNA Using Scanning Tunneling Microscopy. Nature, 346(6281): 294-296 (1990).

In further embodiments, methods of single molecule sequencing known in the art include detecting individual nucleotides as they are incorporated into a primed template, i.e., sequencing by synthesis. Such methods often utilize exonucleases to sequentially release individual fluorescently labeled bases as a second step after DNA polymerase has formed a complete complementary strand. See Goodwin et al., "Application of Single Molecule Detection to DNA Sequencing," Nucleos. Nucleot. 16: 543-550 (1997).

In general, for sequencing methods utilizing compositions of the present invention, individual polymerase compositions are provided within separate discrete regions of a support. For example, in some cases, individual complexes may be provided within individual confinement structures, including nanoscale structures such as nanoscale wells. In further examples, zero-mode waveguide cores or any of the reaction regions discussed above in the stepwise sequencing section serve as the reaction regions for sequencing methods utilizing compositions of the present invention. Examples of waveguides and processes for immobilizing individual complexes therein are described in, e.g., Published International Patent Application No. WO 2007/123763, the full disclosure of which is incorporated herein by reference in its entirety for all purposes and in particular for all teachings related to providing individual complexes into individual confinement structures. In some cases the nucleic acids (e.g., polymerase/template complexes) can be provided onto or proximal to structures or regions that allow for electronic single molecule sequencing. Such structures can include nanoscale electronic structures such as electrodes, capacitors, or field effect transducers (nanoFETs). NanoFETs include those having carbon nanotube gates. Such structures and their use for single molecule sequencing are described, for example, in U.S. Patent Application Publication No. 2015/0065353 which is incorporated herein in its entirety for all purposes and in particular for all teachings related to structures for use in single molecule sequencing.

Incorporation of labeled nucleotide analogs by polymerases is particularly useful in a variety of different nucleic acid analyses, including real-time monitoring of DNA polymerization. The label can itself be incorporated, or more preferably, can be released during incorporation of the analog. For example, analog incorporation can be monitored in real time by monitoring label release during incorporation of the analog by the polymerase. The portion of the analog that is incorporated can be the same as a natural nucleotide, or can include features of the analog that differ from a natural nucleotide.

In general, label incorporation or release can be used to indicate the presence and composition of a growing nucleic acid strand, e.g., providing evidence of template replication/amplification and/or sequence of the template. Signaling from the incorporation can be the result of detecting labeling groups that are liberated from the incorporated analog, e.g., in a solid phase assay, or can arise upon the incorporation reaction. For example, in the case of FRET labels where a bound label is quenched and a free label is not, release of a label group from the incorporated analog can give rise to a fluorescent signal. Alternatively, the enzyme may be labeled with one member of a FRET pair proximal to the active site, and incorporation of an analog bearing the other member will allow energy transfer upon incorporation. The use of enzyme bound FRET components in nucleic acid sequencing applications is described, e.g., in U.S. Patent Application Publication No. 2003/0044781, incorporated herein by reference.

In one example reaction of interest, a polymerase reaction can be isolated within an extremely small observation volume that effectively results in observation of individual polymerase molecules. As a result, the incorporation event provides observation of an incorporating nucleotide analog that is readily distinguishable from non-incorporated nucleotide analogs. In a preferred aspect, such small observation volumes are provided by immobilizing the polymerase enzyme within an optical confinement, such as a Zero Mode Waveguide (ZMW). For a description of ZMWs and their application in single molecule analyses, and particularly nucleic acid sequencing, see, e.g., U.S. Patent Application Publication No. 2003/0044781 and U.S. Pat. No. 6,917,726, each of which is incorporated herein by reference in its entirety for all purposes. See also Levene et al. (2003) "Zero-mode waveguides for single-molecule analysis at high concentrations" Science 299:682-686, Eid et al. (2009) "Real-time DNA sequencing from single polymerase molecules" Science 323:133-138, and U.S. Pat. Nos. 7,056,676, 7,056,661, 7,052,847, and 7,033,764, the full disclosures of which are incorporated herein by reference in their entirety for all purposes.

In general, a polymerase enzyme is complexed with the template strand in the presence of one or more nucleotides and/or one or more nucleotide analogs. For example, in certain embodiments, labeled analogs are present representing analogous compounds to each of the four natural nucleotides, A, T, G and C, e.g., in separate polymerase reactions, as in classical Sanger sequencing, or multiplexed together, e.g., in a single reaction, as in multiplexed sequencing approaches. When a particular base in the template strand is encountered by the polymerase during the polymerization reaction, it complexes with an available analog that is complementary to such nucleotide, and incorporates that analog into the nascent and growing nucleic acid strand. In one aspect, incorporation can result in a label being released, e.g., in polyphosphate analogs, cleaving between the a and 13 phosphorus atoms in the analog, and consequently releasing the labeling group (or a portion thereof). The incorporation event is detected, either by virtue of a longer presence of the analog and, thus, the label, in the complex, or by virtue of release of the label group into the surrounding medium. Where different labeling groups are used for each of the types of analogs, e.g., A, T, G or C, identification of a label of an incorporated analog allows identification of that analog and consequently, determination of the complementary nucleotide in the template strand being processed at that time. Sequential reaction and monitoring permits real-time monitoring of the polymerization reaction and determination of the sequence of the template nucleic acid. As noted above, in particularly preferred aspects, the polymerase enzyme/template complex is provided immobilized within an optical confinement that permits observation of an individual complex, e.g., a zero mode waveguide. For additional information on single molecule sequencing monitoring incorporation of phosphate-labeled analogs in real time, see, e.g., Eid et al. (2009) "Real-time DNA sequencing from single polymerase molecules" Science 323:133-138.

In a first exemplary technique, a nucleic acid synthesis complex, including a polymerase enzyme, a template sequence and a complementary primer sequence, is provided immobilized within an observation region that permits illumination and observation of a small volume that includes the complex without excessive illumination of the surrounding volume. By illuminating and observing only the volume immediately surrounding the complex, one can readily identify fluorescently labeled nucleotides that become incorporated during that synthesis, as such nucleotides are retained within that observation volume by the polymerase for longer periods than those nucleotides that are simply randomly diffusing into and out of that volume. In particular, when a nucleotide is incorporated into DNA by the polymerase, it is retained within the observation volume for a prolonged period of time, and upon continued illumination yields a prolonged fluorescent signal. By comparison, randomly diffusing and not incorporated nucleotides remain within the observation volume for much shorter periods of time, and thus produce only transient signals, many of which go undetected due to their extremely short duration.

In particularly preferred exemplary systems, the confined illumination volume is provided through the use of arrays of optically confined apertures termed zero mode waveguides (ZMWs). See, e.g., U.S. Pat. No. 6,917,726, which is incorporated herein by reference in its entirety for all purposes. For sequencing applications, the DNA polymerase is typically provided immobilized upon the bottom of the ZMW, although another component of the complex (e.g., a primer or template) is optionally immobilized on the bottom of the ZMW to localize the complex. See, e.g., Korlach et al. (2008) PNAS U.S.A. 105(4):1176-1181 and US patent application publication 2008-0032301, each of which is incorporated herein by reference in its entirety for all purposes.

In operation, the fluorescently labeled nucleotides (e.g., analogs corresponding to A, C, G and T) bear one or more fluorescent dye groups on a terminal phosphate moiety that is cleaved from the nucleotide upon incorporation. As a result, synthesized nucleic acids do not bear the build-up of fluorescent labels, as the labeled polyphosphate groups diffuse away from the complex following incorporation of the associated nucleotide, nor do such labels interfere with the incorporation event. See, e.g., Korlach et al. (2008) Nucleosides, Nucleotides and Nucleic Acids 27:1072-1083.

In a second exemplary technique, the immobilized complex and the nucleotides to be incorporated are each provided with interactive labeling components. Upon incorporation, the nucleotide borne labeling component is brought into sufficient proximity to the complex borne (or complex proximal) labeling component, such that these components produce a characteristic signal event. For example, the polymerase may be provided with a fluorophore that provides fluorescent resonant energy transfer (FRET) to appropriate acceptor fluorophores. These acceptor fluorophores are provided upon the nucleotide to be incorporated, where each type of nucleotide bears a different acceptor fluorophore, e.g., that provides a different fluorescent signal. Upon incorporation, the donor and acceptor are brought close enough together to generate energy transfer signal. By providing different acceptor labels on the different types of nucleotides, one obtains a characteristic FRET-based fluorescent signal for the incorporation of each type of nucleotide, as the incorporation is occurring.

In a related aspect, a nucleotide analog may include two interacting fluorophores that operate as a donor/quencher pair, where one member is present on the nucleobase or other retained portion of the nucleotide, while the other member is present on a phosphate group or other portion of the nucleotide that is released upon incorporation, e.g., a terminal phosphate group. Prior to incorporation, the donor and quencher are sufficiently proximal on the same analog as to provide characteristic signal quenching. Upon incorporation and cleavage of the terminal phosphate groups, e.g., bearing a donor fluorophore, the quenching is removed and the resulting characteristic fluorescent signal of the donor is observable.

In exploiting the foregoing processes, where the incorporation reaction occurs too rapidly, it may result in the incorporation event not being detected, i.e., the event speed exceeds the detection speed of the monitoring system. The missed detection of incorporated nucleotides can lead to an increased rate of errors in sequence determination, as omissions in the real sequence. In order to mitigate the potential for missed pulses due to short reaction or product release times, in one aspect, the current invention can result in increased reaction and/or product release times during incorporation cycles. Similarly, very short interpulse distances can occasionally cause pulse merging. An advantage of employing polymerases with reduced reaction rates, e.g., polymerases exhibiting decreased rates and/or two slow-step kinetics as described in US patent application publications 2009-0286245 and 2010-0112645, is an increased frequency of longer, detectable, binding events. This advantage may also be seen as an increased ratio of longer, detectable pulses to shorter, non-detectable pulses, where the pulses represent binding events.

The sequencing processes, e.g., using the substrates described above and the compositions of the invention, are generally exploited in the context of a fluorescence optical system that is capable of illuminating the various complexes on the substrate, and obtaining, detecting and separately recording fluorescent signals from these complexes. Such systems typically employ one or more illumination sources that provide excitation light of appropriate wavelength(s) for the labels being used. An optical train directs the excitation light at the reaction region(s) and collects emitted fluorescent signals and directs them to an appropriate detector or detectors. Additional components of the optical train can provide for separation of spectrally different signals, e.g., from different fluorescent labels, and direction of these separated signals to different portions of a single detector or to different detectors. Other components may provide for spatial filtering of optical signals, focusing and direction of the excitation and or emission light to and from the substrate. An exemplary system is also described in Lundquist et al., Published U.S. Patent Application No. 2007-0036511, Optics Letters, Vol. 33, Issue 9, pp. 1026-1028, the full disclosure of which is incorporated herein by reference in its entirety for all purposes.

Fluorescence reflective optical trains can be used in the applications of the systems of the invention. For a discussion on the advantages of such systems, see, e.g., U.S. patent application Ser. No. 11/704,689, filed Feb. 9, 2007, Ser. No. 11/483,413, filed Jul. 7, 2006, and Ser. No. 11/704,733, filed Feb. 9, 2007, the full disclosures of which are incorporated herein by reference in their entirety for all purposes.

In the context of the nucleic acid sequencing methods described herein, it will be appreciated that the signal sources each represent sequencing reactions, and particularly, polymerase mediated, template dependent primer extension reactions, where in preferred aspects, each base incorporation event results in a prolonged illumination (or localization) of one of four differentially labeled nucleotides being incorporated, so as to yield a recognizable pulse (peak) that carries a distinguishable spectral profile or color.

In further embodiments, methods and compositions of the present invention are utilized in sequencing methods utilizing nanopores. In exemplary embodiments, a single nucleic acid is loaded into each of a plurality of nanopores. In certain embodiments, the nucleic acids are attached proximal to the nanopore. As will be appreciated, helicases and/or exonucleases as well as polymerases can be used in nanopore sequencing. Complexes of these enzymes with nucleic acids can be loaded to nanopores as detailed herein, and the nucleic acid or enzyme component of the complex can be attached to or proximal to the nanopore. Methods of nanopore sequencing are known in the art and disclosed for example in US Published App. Nos. 2013/0327644 and 2014/0051068, which are hereby incorporated by reference for all purposes and in particular for all teachings, written description, figures and figure legends related to nanopore sequencing.

The methods described herein can further include computer implemented processes, and/or software incorporated onto a computer readable medium instructing such processes, as set forth in greater detail below. As such, signal data generated by the reactions and optical systems described above, is input or otherwise received into a computer or other data processor, and subjected to one or more of the various process steps or components set forth below. Once these processes are carried out, the resulting output of the computer implemented processes may be produced in a tangible or observable format, e.g., printed in a user readable report, displayed upon a computer display, or it may be stored in one or more databases for later evaluation, processing, reporting or the like, or it may be retained by the computer or transmitted to a different computer for use in configuring subsequent reactions or data processes.

Computers for use in carrying out the processes of the invention can range from personal computers such as PC or MacIntosh® type computers running Intel Pentium or Duo-Core processors, to workstations, laboratory equipment, or high speed servers, running UNIX, LINUX, Windows®, or other systems. Logic processing of the invention may be performed entirely by general purposes logic processors (such as CPU's) executing software and/or firmware logic instructions; or entirely by special purposes logic processing circuits (such as ASICs) incorporated into laboratory or diagnostic systems or camera systems which may also include software or firmware elements; or by a combination of general purpose and special purpose logic circuits. Data formats for the signal data may comprise any convenient format, including digital image based data formats, such as JPEG, GIF, BMP, TIFF, or other convenient formats, while video based formats, such as avi, mpeg, mov, rmv, or other video formats may be employed. The software processes of the invention may generally be programmed in a variety of programming languages including, e.g., Matlab, C, C++, C#, NET, Visual Basic, Python, JAVA, CGI, and the like.

In some cases, the compositions, methods, and systems of the invention can be used as part of an integrated sequencing system, for example, as described in US 20120014837—Illumination of Integrated Analytical Systems, US 20120021525—Optics Collection and Detection System and Method, US 20120019828—Integrated Analytical System and Method, 61/660,776 filed Jun. 17, 2012—Arrays of Integrated Analytical Devices and Methods for Production, and US 20120085894—Substrates and Optical Systems and Methods of Use Thereof which are incorporated herein by reference in their entirety for all purposes.

In certain embodiments, the sequencing compositions described herein will be provided in whole, or in part, in kit form enabling one to carry out the processes described herein. Such kits will typically comprise one or more components of the reaction complex, such as the polymerase enzyme and primer sequences. Such kits will also typically include buffers and reagents for loading of the polymerase and/or a template as in the processes described herein. The kits will also optionally include other components for carrying out sequencing applications in accordance with those methods described herein. In particular, such kits may include ZMW array substrates for use in observing individual reaction complexes as described herein.

In further exemplary embodiments, kits of the present disclosure include (alone, or in any combination with the above described components of kits) components for use in the loading methods described herein. Such components may include in any combination one or more of the following: one or more nucleic acid condensing agent (e.g., in a prepared solution), standard buffer for covering the surface, high density loading solution, polymerase enzymes, nucleic acid templates, primer sequences, particles for cleaning the high density loading solution, magnetic beads or other particles for loading the nucleic acids, and any other composition described herein associated with loading polymerase compositions to a surface and/or conducting a sequencing reaction.

In addition to the various components set forth above, the kits will typically include instructions for combining the various components in the amounts and/or ratios set forth herein, to carry out the desired processes, as also described or referenced herein, e.g., for performing sequence by incorporation reactions and/or loading methods.

Substrates and Surfaces

Substrates of use in methods of the invention are known in the art and discussed herein, and as will be appreciated, any of the substrates discussed herein can be used in any combination for any embodiments discussed herein.

In exemplary embodiments, methods of the invention utilize substrates that include one or more reaction regions (also referred to herein as "array regions") arranged in the form of an array on an inert substrate material, also referred to herein as a "solid support" or "surface", that allows for combination of reactants (e.g., in a sequencing reaction) in a defined space. Arrays can be regular or irregular, e.g., random. The substrates and array regions can also allow for detection, e.g., of the sequencing reaction event. As described above, nucleic acids or polymerase complexes can be deposited in the reaction regions such that individual nucleic acids (or polymerase reactions) are independently optically observable. A reaction region can be a localized area on the substrate material that facilitates interaction of reactants, e.g., in a nucleic acid sequencing reaction. A reaction region may in certain embodiments be a nanoscale well (also referred to herein as a nanowell), and in further embodiments the nanowell is a ZMW. A nanoscale well typically has dimensions in the nanometer range, i.e., less than 1 micrometer. In some embodiments, a nanoscale well has a cross-sectional diameter of less than 1000, 900, 800, 700, 600, or 500 nm, e.g., less than 400, 350, 300, 250, or 200 nm. In some embodiments, a nanoscale well has a depth of less than 1000, 900, 800, 700, 600, or 500 nm, e.g., less than 400, 350, 300, 250, or 200 nm. As discussed herein, the sequencing reactions contemplated by the invention can in some embodiments occur on numerous individual nucleic acid samples in tandem, in particular simultaneously sequencing numerous nucleic acid samples, e.g., derived from genomic and chromosomal DNA. The apparatus of the invention can therefore include an array having a sufficient number of array regions/reaction regions to carry out such numerous individual sequencing reactions. In one embodiment, the array comprises at least 1,000 reaction regions. In another embodiment, the array comprises greater than 400,000 reaction regions, preferably between 400,000 and 20,000,000 reaction regions. In a more preferred embodiment, the array comprises between 1,000,000 and 16,000,000 reaction regions, e.g., 1,000,000, 2,000,000, 3,000,000, 4,000,000, or 5,000,000 reaction regions.

The reaction regions on the array may take the form of a cavity or well in the substrate material, having a width and depth, into which reactants can be deposited. One or more of the reactants typically are bound to the substrate material in the reaction region and the remainder of the reactants are in a medium which facilitates the reaction and which flows through or contacts the reaction region. When formed as cavities or wells, the chambers are preferably of sufficient dimension and order to allow for (i) the introduction of the necessary reactants into the chambers, (ii) reactions to take place within the chamber and (iii) inhibition of mixing of reactants between chambers. The shape of the well or cavity is preferably circular or cylindrical, but can be multisided so as to approximate a circular or cylindrical shape. In another embodiment, the shape of the well or cavity is substantially hexagonal. The cavity can have a smooth wall surface. In an additional embodiment, the cavity can have at least one irregular wall surface. The cavities can have, e.g., a planar bottom or a concave bottom.

The reaction regions may in some situations take the form of a nanopore. Such reaction regions, including arrays of nanopores, are known in the art and described for example in US Published App. Nos. 2013/0327644 and 2014/0051068, which are hereby incorporated by reference in their entirety for all purposes and in particular for all teachings related to nanopore arrays.

Any material can be used as the solid support material, as long as the surface allows for stable attachment of nucleic acids or polymerase enzyme complexes and optionally detection of nucleotide incorporation. The solid support material can be planar or can be cavitated, e.g., in a cavitated terminus of a fiber optic or in a microwell etched, molded, or otherwise micromachined into the planar surface, e.g. using techniques commonly used in the construction of microelectromechanical systems. See e.g., Rai-Choudhury, HANDBOOK OF MICROLITHOGRAPHY, MICROMACHINING, AND MICROFABRICATION, VOLUME 1: MICROLITHOGRAPHY, Volume PM39, SPIE Press (1997); Madou, CRC Press (1997), Aoki, Biotech. Histochem. 67: 98-9 (1992); Kane et al., Biomaterials. 20: 2363-76 (1999); Deng et al., Anal. Chem. 72:3176-80 (2000); Zhu et al., Nat. Genet. 26:283-9 (2000). In some embodiments, the solid support is optically transparent, e.g., glass.

Suitable substrates include chips having arrays of nanoscale wells or zero mode waveguides. Exemplary substrates include substrates having a metal or metal oxide layer on a silica-based layer, with nanoscale wells disposed through the metal or metal layer to or into the silica-based layer. Such substrates are described, for example in U.S. patent application Ser. Nos. 10/259,268, 14/187,198, 14/107,730, 13/920,037, and U.S. Pat. Nos. 8,994,946, 8,906,670, 8,993,307, 8,802,600, 7,907,800, and 7,302,146, which are incorporated herein by reference in their entirety for all purposes and in particular for all teachings related to substrates.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. Accordingly, the following examples are offered to illustrate, but not to limit, the claimed invention.

Example 1: Flexible Linker in Capture Primer Improves Template Loading

A capture primer as schematically illustrated in FIG. 1, including a six unit PEG spacer (FIG. 2A) separating and connecting a bead-capture poly-A tail and a priming region complementary to the DNA template, is produced. An equivalent control primer lacking the PEG spacer is also produced. A symmetric 11 kb SMRTbell™ template (including a double-stranded central region and two identical single-stranded hairpin end regions) is complexed with DNA polymerase and primer, bound to magnetic beads coated with poly-T, and loaded into ZMWs using a dynamic magnetic field as described above and in U.S. Pat. No. 8,715,930.

Figure 3:
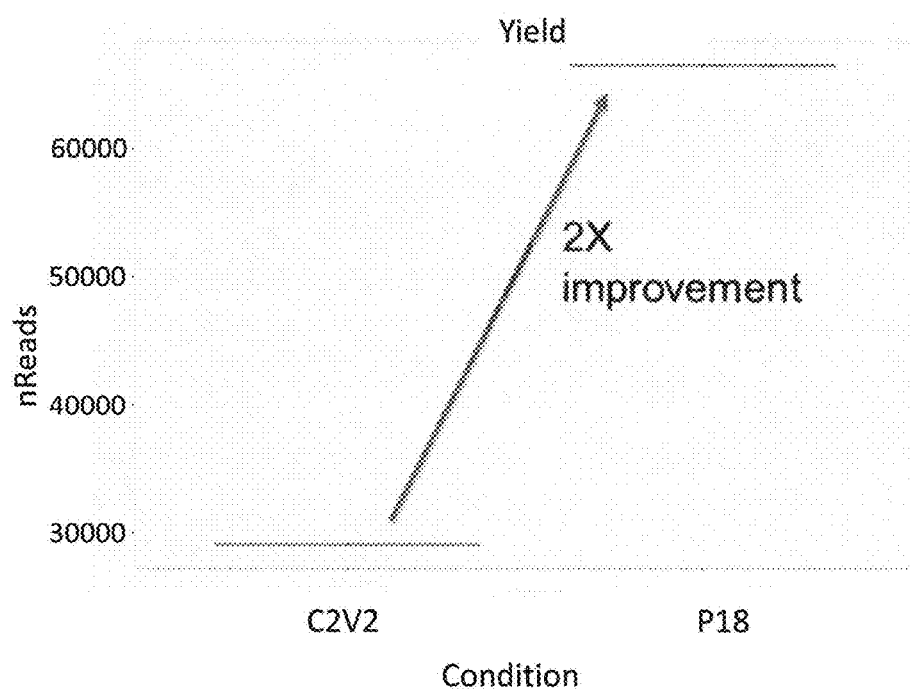
FIG. 3 shows data on the number of empty versus productively singly loaded ZMWs for loading of a complex including an 11 kb symmetric SMRTbell™ template and either a primer including a flexible PEG linker (P18) or a control primer lacking the linker (C2V2).

The capture primer including the six unit PEG spacer (18 atoms, P18) exhibits improved DNA immobilization in sequencing experiments. As shown in FIG. 3, the number of productively singly loaded ZMWs is greater when a capture primer including a P18 spacer is employed than when a capture primer lacking any spacer (C2V2) is employed with an 11 kb symmetric SMRTbell™ template. Inclusion of the P18 spacer increases the number of ZMWs loaded with a mixture again greatly increases the number of ZMWs loaded. At equivalent input amounts (30 fmole), a greater than 20-fold increase in loading is observed for the PEG condition as for the control lacking PEG.

TABLE 1

Loading of a 15 kb E. coli library with PEG and modified linker-primer.

| Analysis Metric | PEG 7.5 fm | PEG 15 fm | PEG 30 fm | Control 30 fm |
| --- | --- | --- | --- | --- |
| SMRTLink job id | 26656 | 26665 | 26708 | 26709 |
| Mean Mapped Concordance | 0.8354 | 0.8313 | 0.8299 | 0.8355 |
| Number of Subreads (mapped) | 175879 | 430954 | 350259 | 14866 |
| Number of Subread Bases (mapped) | 1.56 GB | 3.60 GB | 3.00 GB | 0.105 GB |
| Subread Length Mean (mapped) | 8869 | 8363 | 8556 | 7115 |
| Subread Length N50 (mapped) | 14807 | 13905 | 14126 | 12601 |
| Subread Length 95% (mapped) | 22570 | 21670 | 21900 | 20170 |
| Subread Length Max (mapped) | 38363 | 43486 | 39509 | 36474 |
| Number of Polymerase Reads (mapped) | 160946 | 389639 | 320428 | 13834 |
| Polymerase Read Length Mean (mapped) | 9706 | 9265 | 9368 | 7659 |
| Polymerase Read N50 (mapped) | 16164 | 15437 | 15440 | 13550 |
| Polymerase Read Length 95% (mapped) | 26210 | 25230 | 25310 | 23160 |
| Polymerase Read Length Max (mapped) | 47805 | 46437 | 45076 | 40133 | single polymerase-template complex and yielding sequencing data by more than twofold, from 19% to 43%.

Example 2: Nucleic Acid Condensing Agent Facilitates Magbead Loading

Figure 4:
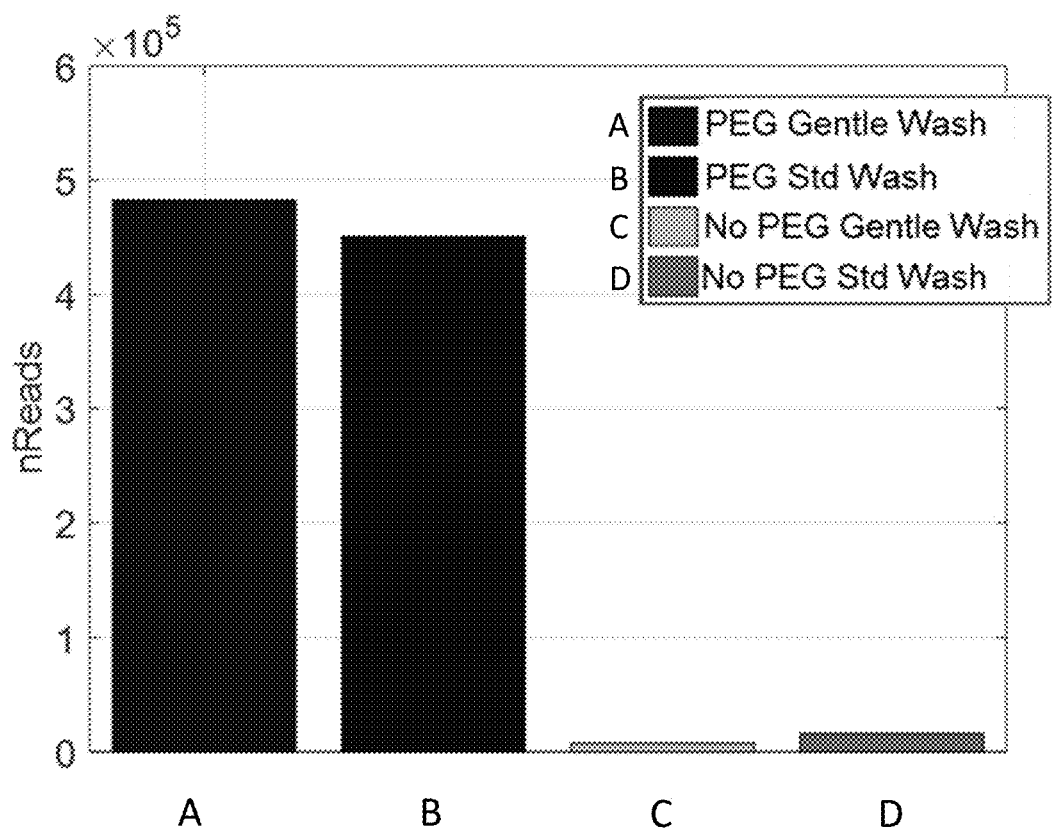
FIG. 4 shows a graph comparing results for sequencing runs including or lacking PEG in the immobilization mixture under two different wash conditions.

As shown in FIG. 4 and Table 1, inclusion of PEG during immobilization of the nucleic acid-polymerase complex greatly increases the number of productively loaded ZMWs. SMRTbell template is annealed with a P18 primer (described hereinabove), complexed with polymerase, and captured to magnetic beads according to published protocols for MagBeads (Pacific Biosciences of California), except that beads are washed prior to addition of sample using Mag-Bead Binding Buffer and are washed twice after sample addition with MagBead Wash Buffer, followed by resuspension in MagBead Binding Buffer. Sequencing is performed on a Sequel™ System (Pacific Biosciences of California) according to published protocols, with the following change: dilution buffer is replaced with dilution buffer containing PEG 8000 (at twice the desired final concentration) and potassium acetate. Briefly, the dilution buffer containing PEG is added to the ZMW chip. The suspension of magnetic beads with attached DNA polymerase complex is then added to the chip; at this point, the mixture on the chip contains 250 mM potassium acetate and 8% w/v PEG 8000. Mixing is performed by robot on chip, and the chip is moved to a magnetic bead loading station for immobilization.

The graph shown in FIG. 4 includes results for sequencing runs (120 minute movies) employing two different wash conditions, standard and gentle. For both types of wash, inclusion of PEG in the immobilization mixture greatly increases the number of ZMWs loaded. For this experiment, 10 fmole of 19 kb symmetric SMRTbell™ template complexed with a ten-fold excess of primer and polymerase is loaded per chip, with 120 minute loading time.

Figure 5A:
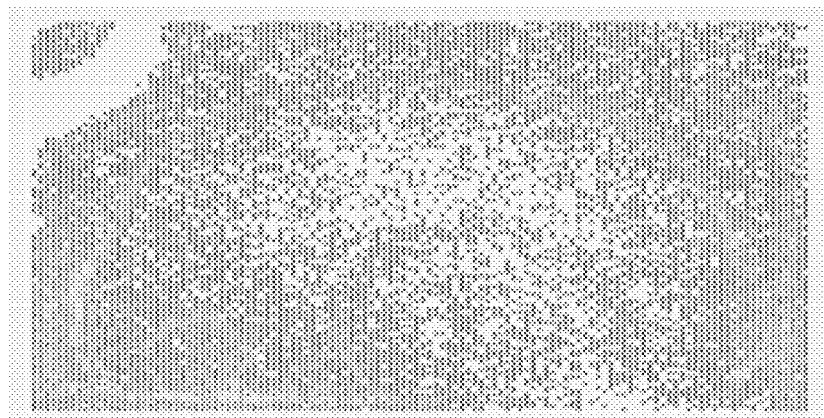
FIG. 5A shows a heatmap illustrating nonuniformity of loading of a chip under control conditions.
Figure 5B:
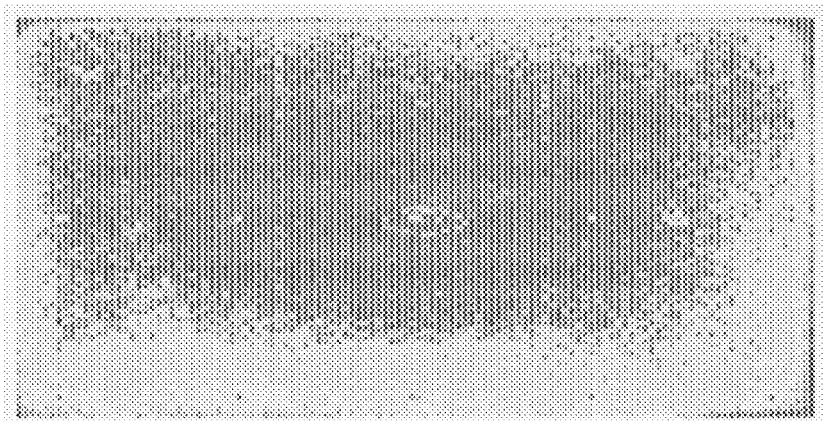
FIG. 5B shows a heatmap illustrating improved loading uniformity of a chip with PEG in the immobilization mixture. Number of sequencing ZMWs out of 80 total bins is shown. Darker colors generally indicate higher numbers of sequencing ZMWs while white indicates low loading.

In another experiment, 7.5, 15, or 30 fmole of a 15 kb E. coli SMRTbell™ library is loaded per chip. As seen in Table 1, 39% loading of the 15 kb library is observed at 15 fmole of sample input. Inclusion of PEG in the immobilization In addition to increasing the number of ZMW wells productively loaded, inclusion of PEG also improves the uniformity of DNA immobilization. Without limitation to any particular mechanism, PEG efficiently prevents surface drying during immobilization and subsequent washing steps, and this reduces DNA loss and polymerase deactivation during such drying events. This also improves the overall immobilization performance. See the data presented in FIGS. 5A and 5B; note the under-loaded area in the center of the control chip (FIG. 5A). With PEG, the center part of the chip is uniformly loaded (FIG. 5B).

Example 3: Nucleic Acid Condensing Agent Improves Template Binding to Beads

Bead binding efficiency of SMRTbells™ with different sized inserts is measured in the presence or absence of PEG. BWB indicates MagBead Wash Buffer; BWB-PEG is a comparable buffer including 12.5 mM PEG 8000, 400 mM potassium acetate, and 0.05 mM strontium acetate.

TABLE 2

Bead binding efficiency (% DNA recovered on beads)

| | 48k λ | 30k E. coli | 19k | 15k E. coli |
| --- | --- | --- | --- | --- |
| BWB | 45% | 69% | 62% | 79% |
| BWB-PEG | >98%** | >98% | >98% | >98% |

**The DNA in solution after beading is too low to be accurately measured by Qubit™ fluorometry.

As seen in Table 2, almost all of the DNA of all sizes is captured on beads with PEG present in the buffer, while DNA recovery in the absence of PEG is lower and appears to be correlated with insert size (where larger size generally reduces recovery).

Figure 7:
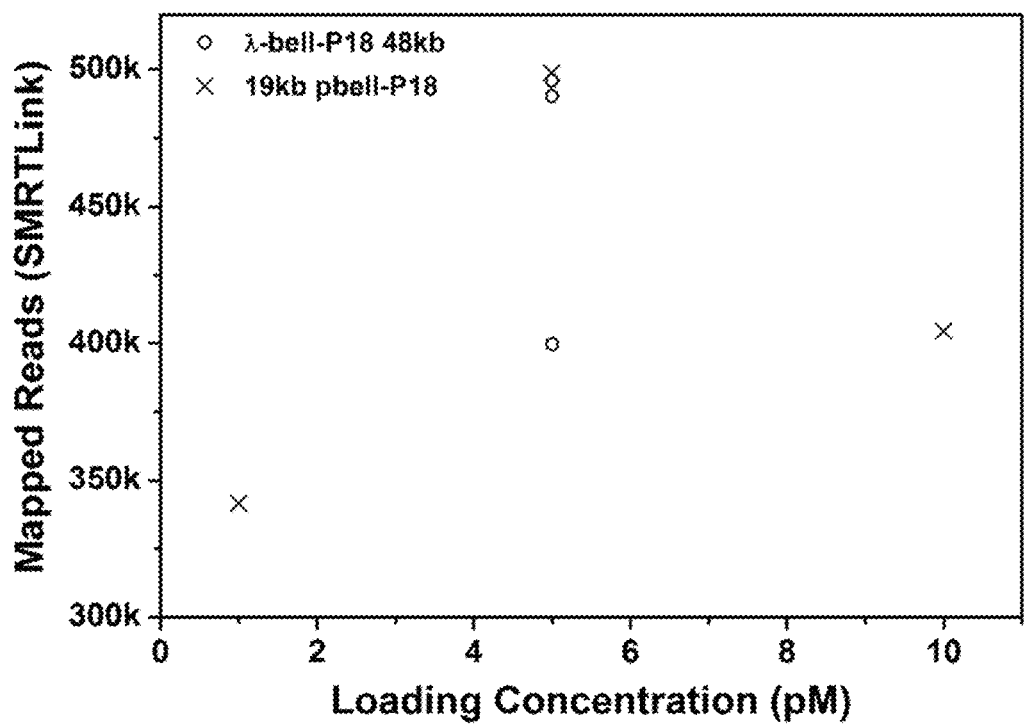
FIG. 7 presents data from diffusion loading of large DNA templates into ZMWs at low picomolar concentrations in the presence of PEG.

Example 4: Nucleic Acid Condensing Agent Facilitates Diffusion Loading of Large Templates As shown in FIG. 7, inclusion of a nucleic acid condensing agent during immobilization of polymerase-template complexes facilitates loading of large DNA templates into ZMWs at low picomolar concentrations. Templates are SMRTbells™ including either a 19 kb plasmid insert or a 48 kb λ insert. Complexes are formed by incubating one of the templates with a modified Φ29 polymerase and a P18 primer (as described herein) then column cleaned to remove excess primer and/or free polymerase. A Sequel™ chip (Pacific Biosciences of California) is optionally washed three times with 150 µl ethanol, four to five times with 150 µl immobilization buffer, and twice with 100 µl 10 mM PEG 8000, 250 mM potassium acetate, and 0.15 mM strontium acetate in a solution buffered with Tris, pH 8. The polymerase-template sample is diluted into 150 µl final volume of 10 mM PEG 8000, 250 mM potassium acetate, and 0.15 mM strontium acetate, mixed well, dispensed onto the ZMW chip, mixed again on chip, and incubated in a humidity chamber for two hours. The chip is then gently washed and sequencing is performed on a Sequel™ System (Pacific Biosciences of California). Data on sequencing yield (mapped reads, representing the number of ZMWs yielding sequencing data for the indicated template, of the one million on the chip) is shown in FIG. 7. For comparison, diffusion loading of templates of the same sizes at the same concentrations in the absence of a condensing agent would result in negligible or no sequencing yield.

Figure 8:
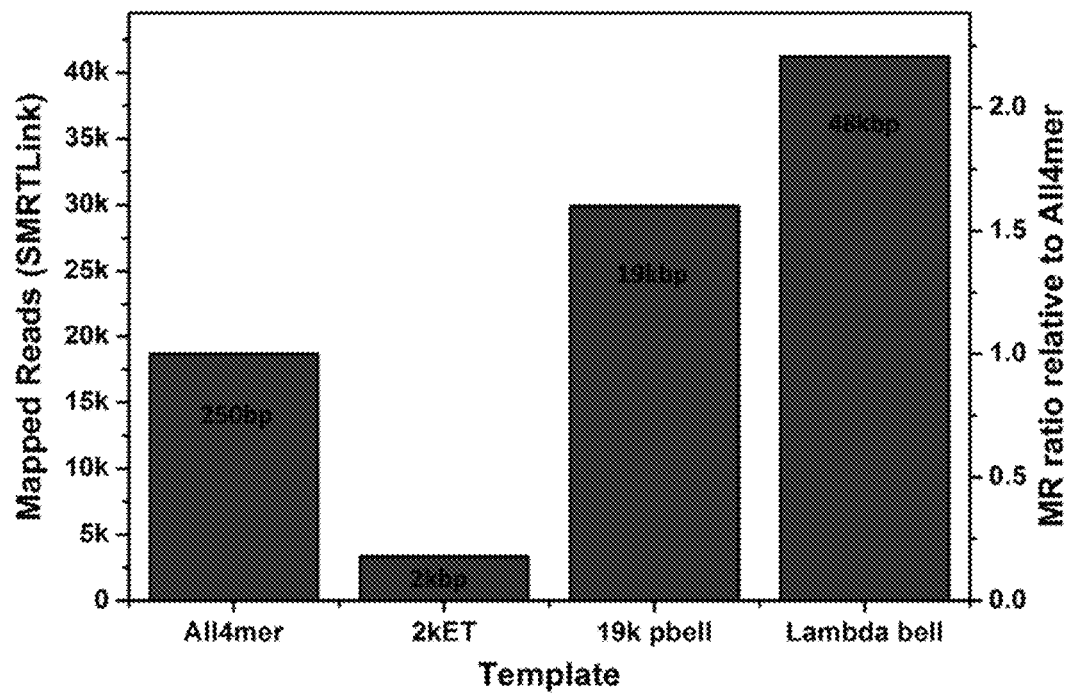
FIG. 8 presents data from diffusion loading of a mixed population of different length templates into ZMWs in the presence of PEG.

Example 5: Nucleic Acid Condensing Agent Improves Loading of Large Templates Over Loading of Small Templates As shown in FIG. 8, inclusion of a nucleic acid condensing agent during immobilization of a mixed population of different length templates improves loading of larger templates. Polymerase-template complexes are formed with four different templates of different sizes, 250 bp, 2 kb, 19 kb, and 48 kb. Equimolar amounts of the four templates are mixed and then added to an equal volume of concentrated PEG solution. The final concentration of each template is 0.5 pM (0.075 fmol) in 150 µl 10 mM PEG 8000, 250 mM potassium acetate, and 0.15 mM strontium acetate buffered with Tris, pH 8. A Sequel™ chip (Pacific Biosciences of California) is washed with PEG solution and then incubated with the mixed sample for one hour. Data on sequencing yield (mapped reads, representing the number of ZMWs yielding sequencing data for the indicated template) is shown in FIG. 8. Loading of the larger 19 and 48 kb templates is favored over the smaller 250 bp and 2 kb templates.

Example 6: Preparation of Double-Stranded Circular Template for Diffusion Loading One or more random or specific nick sites or gap sites are introduced on double-stranded circular DNA (including on a large circular DNA, e.g., a plasmid) using one or more appropriate commercially available endonucleases. Where multiple nicked or gapped sites are introduced into a single DNA molecule, the distance between them is preferably greater than the expected readlength of a subsequent sequencing reaction to ensure that sequencing is not terminated prematurely. The template and polymerase are next incubated together in buffer to allow the polymerase to bind to the nick or gap site. In one example, the template and polymerase are mixed at close to 1:1 ratio or at slight template excess (e.g. 1.5:1) so that at most one polymerase molecule can bind to the nicked or gapped DNA circle. In another example, the polymerase is at high excess relative to the template (e.g. 2:1, 3:1, or 10:1), and remaining free unbound polymerases are removed by a clean-up procedure which can involve, e.g., column filtering, dialysis, magnetic beads, or a combination thereof.

A solution of this template-polymerase complex is then incubated over the ZMW chip in PEG buffer (as described above) so that the compacted template-polymerase complex can load into ZMWs and bind at the bottom surface. In one example, the loading of the template-polymerase complex occurs via diffusion. In another example, the template-polymerase complexes are first captured onto magnetic beads, e.g., by condensation of the nucleic acids on the bead surface in the presence of PEG and cations, and then the bead-bound nucleic acid-polymerase complexes are contacted with the substrate as described above.

At the end of the immobilization step, PEG buffer is washed away and the template can uncondense. DNA extension is initiated using standard SMRT™ sequencing protocol (Pacific Biosciences of California).

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method for distributing polymerase-template complexes into a plurality of nanoscale wells, the method comprising:
   providing a surface comprising the plurality of nanoscale wells;
   contacting polymerase-template complexes in solution with polyethylene glycol (PEG) and a salt comprising a cation to compact the templates of the polymerase-template complexes, thereby providing a solution comprising compacted polymerase-template complexes, wherein the templates of the polymerase-template complexes are at least 5 kb in length, wherein the compacted polymerase-template complexes have a diameter of less than 200 nm, and wherein the compacted polymerase-template complexes are not bound to beads; and
   exposing the surface to the solution, whereby the compacted polymerase-template complexes diffuse into the nanoscale wells, thereby distributing the compacted polymerase-template complexes into the nanoscale wells.

2. The method of claim 1, wherein the solution comprises PEG 8000.

3. The method of claim 1, wherein the solution comprises 2.5-25 mM PEG 8000.

4. The method of claim 1, wherein the solution comprises 5-15 mM PEG 8000.

5. The method of claim 1, wherein the solution comprises a monovalent cation at 50 to 500 mM.

6. The method of claim 1, wherein the solution comprises a monovalent cation at 100 to 300 mM.

7. The method of claim 1, wherein the solution comprises a divalent cation at 0.05 to 10 mM.

8. The method of claim 1, wherein the solution comprises PEG 8000 and K⁺.

9. The method of claim 1, wherein the solution comprises PEG 8000, K⁺, and $Sr^{2+}$.

10. The method of claim 1, wherein the solution comprises 5-15 mM PEG 8000 and 100-300 mM K⁺.

11. The method of claim 1, wherein the nanoscale wells comprise zero mode waveguides (ZMWs).

12. The method of claim 1, wherein the templates of the polymerase-template complexes are at least about 10 kb in length.

13. The method of claim 1, wherein the templates of the polymerase-template complexes are at least about 20 kb in length.

14. The method of claim 1, comprising immobilizing the polymerase-template complexes in the nanoscale wells.

15. The method of claim 1, wherein the nanoscale wells comprise a coupling agent at their bases, wherein the polymerase-template complexes diffuse through the solution to the bases of the nanoscale wells and bind to the coupling agent, thereby immobilizing the polymerase-template complexes in the nanoscale wells.

16. The method of claim 15, wherein the templates in the polymerase-template complexes are of different lengths, at least one of which lengths is greater than 10 kb; wherein the percentage of nanoscale wells occupied by immobilized templates whose length is greater than 10 kb is equal to or greater than the percentage of templates in the initial solution whose length is greater than 10 kb.

17. The method of claim 15, wherein the templates in the polymerase-template complexes comprise a first template whose length is at least 20 times the length of a second template, wherein a ratio of immobilized first template to immobilized second template is equal to or is greater than a ratio of first template to second template in the initial solution.

18. The method of claim 1, comprising immobilizing the polymerase-template complexes in the nanoscale wells, wherein after the immobilizing step at least 38% of the nanoscale wells are occupied by a single immobilized polymerase-template complex.

19. The method of claim 1, wherein the compacted polymerase-template complexes have a diameter of less than 150 nm.

20. The method of claim 1, wherein the contacting step is performed prior to the exposing step.

21. The method of claim 1, wherein the templates of the polymerase-template complexes are at least 10 kb in length, and wherein the compacted polymerase-template complexes have a diameter of less than 150 nm.

22. The method of claim 1, wherein the templates of the polymerase-template complexes comprise a double-stranded central region that is at least 5 kb in length and two single-stranded hairpin end regions.

23. The method of claim 22, wherein the two single-stranded hairpin end regions are identical.

* * * * *